(12) United States Patent
Oron et al.

(10) Patent No.: US 9,764,146 B2
(45) Date of Patent: Sep. 19, 2017

(54) EXTRACORPOREAL IMPLANT CONTROLLERS

(71) Applicant: Bluewind Medical Ltd., Herzliya (IL)

(72) Inventors: Guri Oron, Tel Aviv (IL); Yossi Gross, Moshav Mazor (IL); Eran Benjamin, Tel Aviv (IL); Anton Plotkin, Tel Aviv (IL)

(73) Assignee: BLUEWIND MEDICAL LTD., Herzliya (IL)

( * ) Notice: Subject to any disclaimer, the term of this patent is extended or adjusted under 35 U.S.C. 154(b) by 115 days.

(21) Appl. No.: 14/601,626

(22) Filed: Jan. 21, 2015

(65) Prior Publication Data

US 2016/0206890 A1    Jul. 21, 2016

(51) Int. Cl.
*A61N 1/00* (2006.01)
*A61N 1/372* (2006.01)
(Continued)

(52) U.S. Cl.
CPC ....... *A61N 1/37229* (2013.01); *A61N 1/3787* (2013.01); *A61N 1/36071* (2013.01); *A61N 1/36125* (2013.01); *A61N 1/37205* (2013.01)

(58) Field of Classification Search
CPC .............. A61N 1/3787; A61N 1/37229; A61N 1/36125; A61N 1/37205
(Continued)

(56) References Cited

U.S. PATENT DOCUMENTS 3,411,507 A    11/1968    Wingrove
3,693,625 A     9/1972    Auphan
(Continued)

FOREIGN PATENT DOCUMENTS

DE    102008054403 A1    6/2010
EP        0 688 577       12/1995
(Continued)

OTHER PUBLICATIONS

Brindley (1983) A technique for anodally blocking large nerve fibers.
(Continued)

*Primary Examiner* — Amanda Patton
*Assistant Examiner* — Philip C Edwards
(74) *Attorney, Agent, or Firm* — Sughrue Mion, PLLC

(57) ABSTRACT

Apparatus, comprising (1) a first controller comprising at least one first-controller antenna configured to transmit a first wireless power signal having a first signal power; and a first-controller control unit configured to use battery power to drive the first-controller antenna; (2) a second controller, comprising at least one second-controller antenna, configured to transmit a second wireless power signal having a second signal power; and a second-controller control unit, configured to use mains electricity power to drive the second-controller antenna; and (3) an implant, comprising one or more electrodes; at least one implant antenna configured to receive 1-10 percent of the first signal power, and to receive 0.01-1 percent of the second signal power; and circuitry configured to drive the one or more electrodes responsively to the received 1-10 percent of the first signal power, or the received 0.01-1 percent of the second signal power.

16 Claims, 10 Drawing Sheets

(51) Int. Cl.
*A61N 1/378* (2006.01)
*A61N 1/36* (2006.01)

(58) Field of Classification Search
USPC .......................................................... 607/60
See application file for complete search history.

(56) References Cited

U.S. PATENT DOCUMENTS

| | | |
|---|---|---|
| 4,019,518 A | 4/1977 | Maurer et al. |
| 4,338,945 A | 7/1982 | Kosugi et al. |
| 4,392,496 A | 7/1983 | Stanton |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lue |
| 4,808,157 A | 2/1989 | Coombs |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,411,535 A | 5/1995 | Fujii et al. |
| 5,423,872 A | 6/1995 | Cigaina |
| 5,439,938 A | 8/1995 | Snyder et al. |
| 5,454,840 A | 10/1995 | Krakovsky et al. |
| 5,487,760 A | 1/1996 | Villafana |
| 5,505,201 A | 4/1996 | Grill, Jr. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,083,249 A | 7/2000 | Familoni |
| 6,086,525 A | 7/2000 | Davey et al. |
| 6,091,977 A | 7/2000 | Tarjan et al. |
| 6,091,992 A | 7/2000 | Bourgeois |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Hill et al. |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,496,729 B2 | 12/2002 | Thompson |
| 6,496,730 B1 | 12/2002 | Kleckner et al. |
| 6,582,441 B1 | 6/2003 | He et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,735,474 B1 | 5/2004 | Loeb et al. |
| 6,770,022 B2 | 8/2004 | Mechlenburg |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,149,575 B2 | 12/2006 | Ostroff et al. |
| 7,177,698 B2 | 2/2007 | Klosterman et al. |
| 7,212,867 B2 | 5/2007 | Venrooij et al. |
| 7,228,178 B2 | 6/2007 | Carroll |
| 7,277,749 B2 | 10/2007 | Gordon et al. |
| 7,289,853 B1 | 10/2007 | Campbell et al. |
| 7,324,852 B2 | 1/2008 | Barolat et al. |
| 7,324,853 B2 | 1/2008 | Ayal |
| 7,389,145 B2 | 6/2008 | Kilgore et al. |
| 7,483,752 B2 | 1/2009 | Von arx et al. |
| 7,502,652 B2 | 3/2009 | Gaunt et al. |
| 7,532,932 B2 | 5/2009 | Denker et al. |
| 7,536,226 B2 | 5/2009 | Williams |
| 7,628,750 B2 | 12/2009 | Cohen |
| 7,630,771 B2 | 12/2009 | Cauller |
| 7,634,313 B1 | 12/2009 | Kroll et al. |

(56) References Cited

U.S. PATENT DOCUMENTS

| | | |
|---|---|---|
| 7,655,014 B2 | 2/2010 | Ko et al. |
| 7,657,311 B2 | 2/2010 | Bardy et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,711,434 B2 | 5/2010 | Denker et al. |
| 7,736,379 B2 | 6/2010 | Ewers et al. |
| 7,780,625 B2 | 8/2010 | Bardy |
| 7,797,050 B2 | 9/2010 | Libbus et al. |
| 7,848,818 B2 | 12/2010 | Barolat et al. |
| 7,917,226 B2 | 3/2011 | Nghiem |
| 7,937,148 B2 | 5/2011 | Jacobson |
| 7,941,218 B2 | 5/2011 | Sambelashvili et al. |
| 7,974,706 B2 | 7/2011 | Moffitt et al. |
| 7,991,467 B2 | 8/2011 | Markowitz et al. |
| 7,996,089 B2 | 8/2011 | Haugland et al. |
| 7,996,092 B2 | 8/2011 | Mrva et al. |
| 8,019,443 B2 | 9/2011 | Scheicher et al. |
| 8,055,350 B2 | 11/2011 | Roberts |
| 8,075,556 B2 | 12/2011 | Betts |
| 8,090,438 B2 | 1/2012 | Bardy et al. |
| 8,115,448 B2 | 2/2012 | John |
| 8,131,377 B2 | 3/2012 | Shhi et al. |
| 8,170,675 B2 | 5/2012 | Alataris et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,255,057 B2 | 8/2012 | Fang et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,396,559 B2 | 3/2013 | Alataris et al. |
| 8,428,748 B2 | 4/2013 | Alataris et al. |
| 8,463,404 B2 | 6/2013 | Levi et al. |
| 8,509,905 B2 | 8/2013 | Alataris et al. |
| 8,509,906 B2 | 8/2013 | Walker et al. |
| 8,554,326 B2 | 10/2013 | Alataris et al. |
| 8,634,927 B2 | 1/2014 | Olson et al. |
| 8,649,874 B2 | 2/2014 | Alataris et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,755,893 B2 | 6/2014 | Gross et al. |
| 8,768,472 B2 | 7/2014 | Fang et al. |
| 8,774,926 B2 | 7/2014 | Alataris et al. |
| 8,788,045 B2 | 7/2014 | Gross et al. |
| 8,792,988 B2 | 7/2014 | Alataris et al. |
| 8,849,410 B2 | 9/2014 | Walker et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0176898 A1 | 9/2003 | Gross et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0167584 A1 | 8/2004 | Carroll et al. |
| 2004/0249431 A1 | 12/2004 | Ransbury et al. |
| 2004/0254624 A1 | 12/2004 | Johnson |
| 2005/0131495 A1* | 6/2005 | Parramon ......... A61N 1/37223 607/61 |
| 2005/0143789 A1 | 6/2005 | Whitehurst |
| 2005/0165457 A1 | 7/2005 | Benser et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman |
| 2007/0073354 A1 | 3/2007 | Knudson et al. |
| 2007/0083240 A1 | 4/2007 | Peterson et al. |
| 2007/0173893 A1 | 7/2007 | Pitts |
| 2008/0009914 A1 | 1/2008 | Buysman et al. |
| 2008/0021336 A1 | 1/2008 | Dobak |
| 2008/0027513 A1 | 1/2008 | Carbunaru |
| 2008/0039915 A1 | 2/2008 | Van Den Biggelaar |
| 2008/0103407 A1 | 5/2008 | Bolea et al. |
| 2008/0103572 A1 | 5/2008 | Gerber |
| 2008/0119911 A1 | 5/2008 | Rosero |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0204170 A1 | 8/2009 | Hastings et al. |
| 2009/0204173 A1 | 8/2009 | Fang et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukhovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0280568 A1 | 11/2010 | Bulkes et al. |
| 2010/0305392 A1 | 12/2010 | Gross et al. |
| 2010/0312320 A1 | 12/2010 | Faltys et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0137365 A1 | 6/2011 | Ben-Ezra et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0230922 A1 | 9/2011 | Fishel |
| 2011/0270339 A1 | 11/2011 | Murray, III et al. |
| 2011/0282412 A1 | 11/2011 | Glukhovsky et al. |
| 2011/0301670 A1 | 12/2011 | Gross et al. |
| 2012/0004709 A1* | 1/2012 | Chen ................. A61N 1/37223 607/61 |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0296389 A1 | 11/2012 | Fang et al. |
| 2013/0006326 A1 | 1/2013 | Ackermann et al. |
| 2013/0066393 A1 | 3/2013 | Gross et al. |
| 2014/0214134 A1 | 7/2014 | Peterson |
| 2015/0018728 A1 | 1/2015 | Gross et al. |
| 2015/0080979 A1 | 3/2015 | Lasko et al. |

(56) References Cited

U.S. PATENT DOCUMENTS

| | | | |
|---|---|---|---|
| 2015/0100109 A1 | 4/2015 | Feldman et al. | |
| 2015/0258339 A1 | 9/2015 | Burchiel et al. | |
| 2015/0335882 A1 | 11/2015 | Gross et al. | |

FOREIGN PATENT DOCUMENTS

| | | |
|---|---|---|
| EP | 1533000 | 5/2005 |
| WO | 98/10832 | 3/1998 |
| WO | 99/26530 | 6/1999 |
| WO | 01/10375 | 2/2001 |
| WO | 01/10432 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/106884 A1 | 7/2013 |
| WO | 2013/111137 | 8/2013 |
| WO | 2013/156038 A1 | 10/2013 |
| WO | 2013/164829 | 11/2013 |
| WO | 2014081978 | 5/2014 |
| WO | 2014/087337 | 6/2014 |
| WO | 2014167568 | 10/2014 |
| WO | 2015004673 | 1/2015 |
| WO | 2016/172109 A1 | 10/2016 |

OTHER PUBLICATIONS

DJOGlobal.com—Interferential Current Therapy (IFC).
U.S. Appl. No. 60/985,353, filed Nov. 5, 2007.
electrotherapy.org—Interferential Therapy.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Reggiani et al. "Biophysical effects of high frequency electrical field on muscle fibers in culture." (2009) pp. 49-56.
Sinan Filiz, Luke Xie, Lee E. Weiss, O.B. Ozdoganlar, Micromilling of microbarbs for medical implants, International Journal of Machine Tools and Manufacture, vol. 48, Issues 3-4, Mar. 2008, pp. 459-472.
UCLA Team Reports Initial Success with Trigeminal Nerve Stimulation epilepsy. https://web.archive.org/web/20121020145122/ https:/www.epilepsy.com/epilepsy/newsletter/apr09_STIM.
Szmurlo, R., Starzynski, J., Wincenciak, S. and Rysz, A. (2009) 'Numerical model of vagus nerve electrical stimulation', COMPEL—*The international journal for computation and mathematics in electrical and electronic engineering*, 28(1), pp. 211-220.
An Office Action dated Aug. 8, 2016, which issued during the prosecution of U.S. Appl. No. 14/735,741.
Kucklick, Theodore R., ed. *The medical device R&D handbook.* Chapter 3—Intro to needles and cannulae. CRC Press, 2012.
C. de Balthasar, G. Cosendai, M. Hansen, D. Canfield, L. Chu, R. Davis, and J. Schulman, "Attachment of leads to RF-BION® microstimulators." Jul. 2005.

D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.
G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.
G.E. Loeb, F.J. Richmond, and L.L. Baker, "The BION devices: injectable interfaces with peripheral nerves and muscles," Neurosurgical focus, vol. 20, 2006, pp. 1-9.
E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.
A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.
A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.
A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.
A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.
W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.
W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.
P.R. Troyk, "Injectable electronic identification, monitoring, and stimulation systems," Biomedical Engineering, vol. 1, 1999, p. 177.
T.K. Whitehurst, J.H. Schulman, K.N. Jaax, and R. Carbunaru, "The Bion® Microstimulator and its Clinical Applications," Implantable Neural Prostheses 1, 2009, pp. 253-273.
D.J. Young, "Wireless powering and data telemetry for biomedical implants," Engineering in Medicine and Biology Society, 2009. EMBC 2009. Annual International Conference of the IEEE, 2009, pp. 3221-3224.
Reid R. Harrison, et al., "Wireless Neural Recording with Single Low-Power Integrated Circuit", IEEE Trans Neural Syst Rehabil Eng. Aug. 2009; 17(4): 322-329.
An International Search Report and a Written Opinion both dated Apr. 17, 2012 which issued during the prosecution of Applicant's PCT/IL11/00870.
Patents Galore: Implantable Neurostimulators Fight Snoring and Corpse Eye-Proof Scanners. Printout from http://medgadget.com/ 2006/03/patents_galore.html (Downloaded Jan. 2012).
Chris Seper, "Neuros Medical Launches to Develop New Device to Block Amputee, Chronic Pain", Mar. 16, 2009.
Urgent® PC, Simple. Safe. Effective. Neuromodulation System, Uroplasty, Mar. 2009.
"JumpStart and Case Technology Ventures Invest in Neuros Medical", CTV Case Technology Ventures, Mar. 17, 2009.
"Responses to median and tibial nerve stimulation in patients with chronic neuropathic pain", by Theuvenet, Brain Topography, vol. 11, No. 4, 1999, pp. 305-313(9)—an abstract.

(56) References Cited

OTHER PUBLICATIONS

Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/005069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, Ed M.A. Arbib MIT Press pp. 696-701, 1998.
Epilepsy center. http://www.bcm.tmc.edu/neural/struct/epilep/epilpsy_vagus.html. May 31, 2011 (2 Versions).
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
Mortimer et al., Peripheral Nerve and Muscle Stimulation, Neuroprosthetics Theory and Practice, Chapter 4.2, 2004, p. 632-638.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
An International Search Report and a Written Opinion both dated Jul. 11, 2013, which issued during the prosecution of Applicant's PCT/IL2013/050069.
An International Search Report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
A Notice of Allowance dated Apr. 25, 2014, which issued during the prosecution of U.S. Appl. No. 13/528,433.
A Notice of Allowance dated Jun. 9, 2014, which issued during the prosecution of U.S. Appl. No. 12/796,102.
An Office Action dated Sep. 26, 2013, which issued during the prosecution of U.S. Appl. No. 13/528,433.
Takahata, K.; DeHennis, A.; Wise, K.D.; Gianchandani, Y.B., "Stentenna: a micromachined antenna stent for wireless monitoring of implantable microsensors," in Engineering in Medicine and Biology Society, 2003. Proceedings of the 25th Annual International Conference of the IEEE , vol. 4, No., pp. 3360-3363 vol. 4, 17-21.
Spinal Cord Stimulation advanced level (Mayfield clinic)—dated Feb. 2010.
Kaszala, K. and Ellenbogen, K.A., 2010. Device sensing sensors and algorithms for pacemakers and implantable cardioverter defibrillators. Circulation, 122(13), pp. 1328-1340.
Zhang, D., Zhang, Z., Zi, Z., Zhang, Y., Zeng, W. and Chu, P.K., 2008. Fabrication of graded TiN coatings on nitinol occluders and effects on in vivo nickel release. Bio-medical materials and engineering, 18(6), pp. 387-393.

(56) References Cited

OTHER PUBLICATIONS

Itchkawitz—OC TechInnovation Blog—Electrodes for implantable defibrillator. Printout from http://octechinnovation.com/tag/cameron-health (Downloaded Mar. 2012).
Ebrish, M. et al., Cardiovascular stents as antennas for implantable wireless applications—presentation. BMEN 5151, Apr. 2010.
Abkenari, Lara Dabiri, et al. "Clinical experience with a novel subcutaneous implantable defibrillator system in a single center." Clinical Research in Cardiology 100.9 (2011): 737-744.
An Office Action dated Dec. 12, 2016, which issued during the prosecution of U.S. Appl. No. 14/939,418.
An Extended European Search Report in European Patent Application 16196878.9 dated Feb. 3, 2017.

* cited by examiner

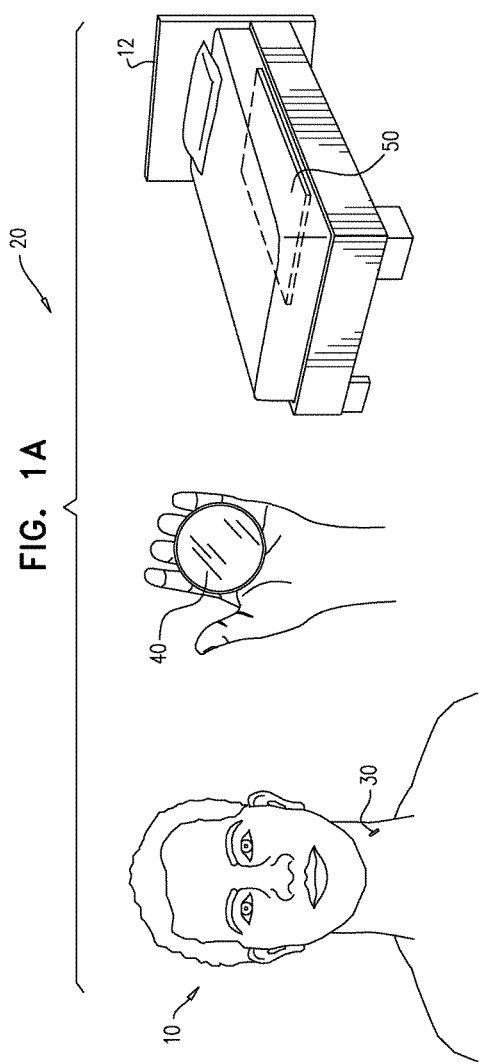

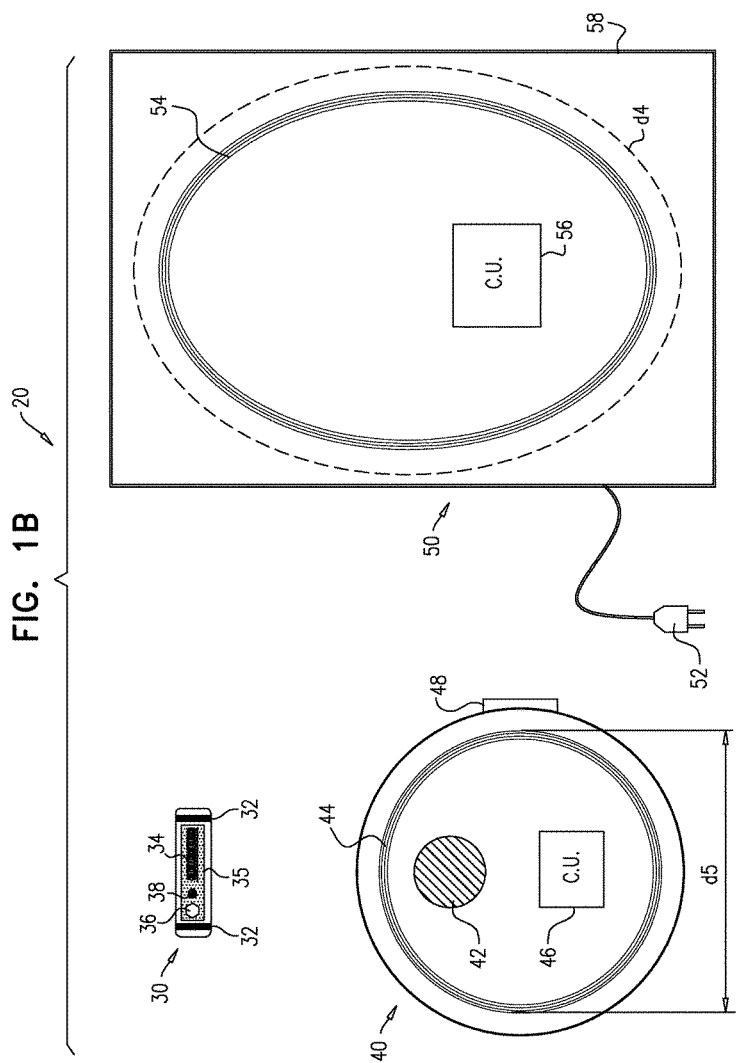

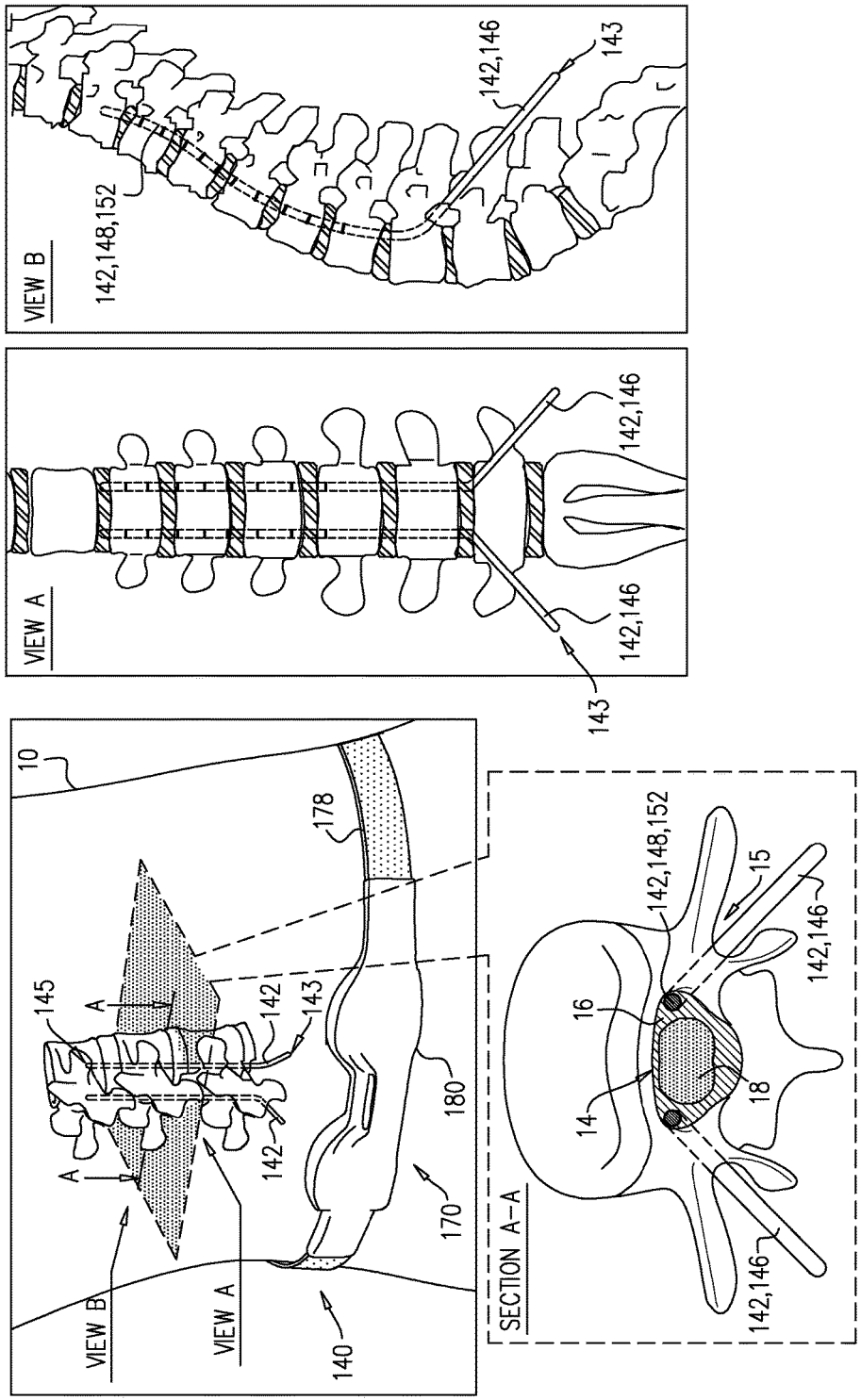

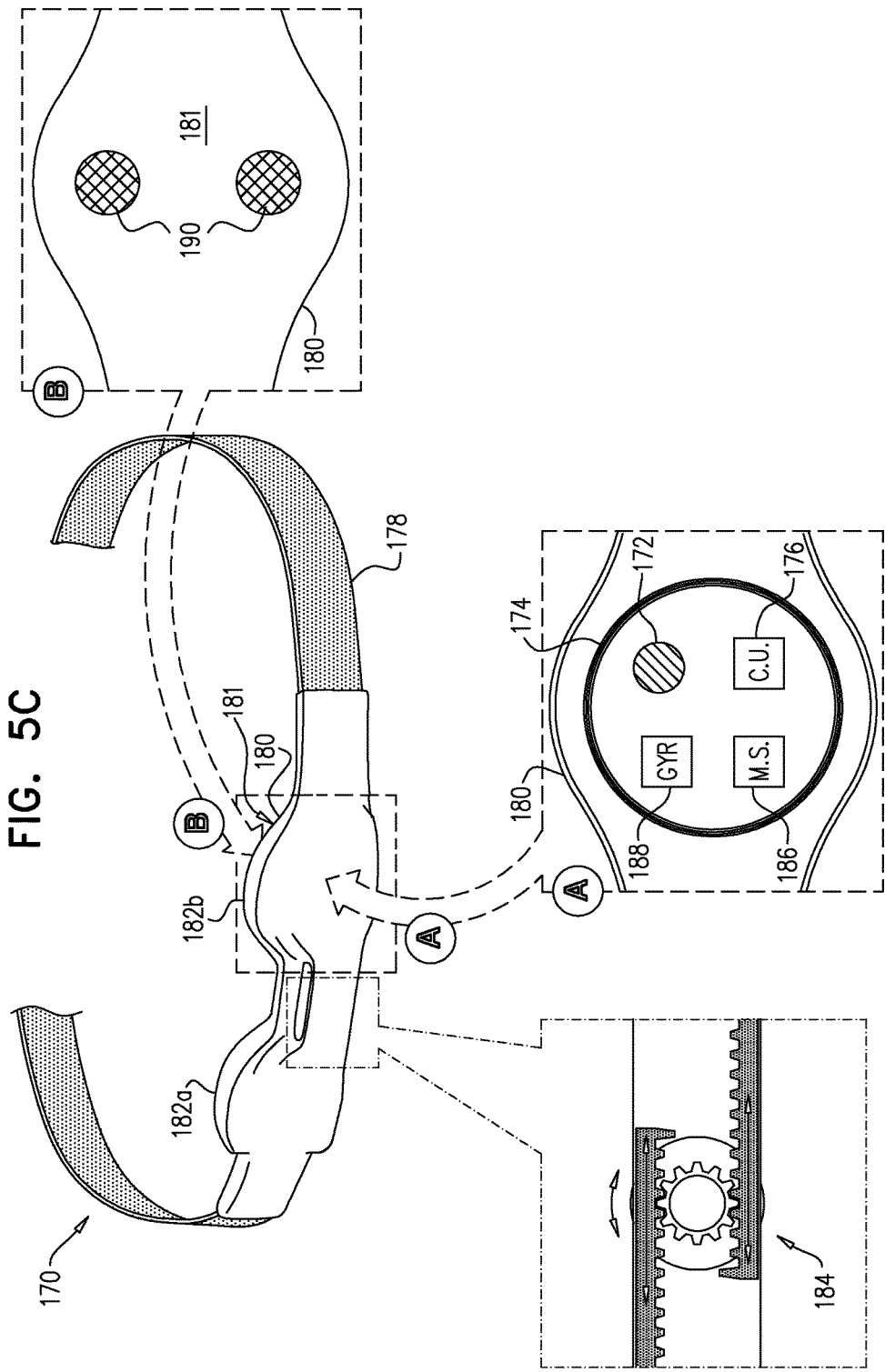

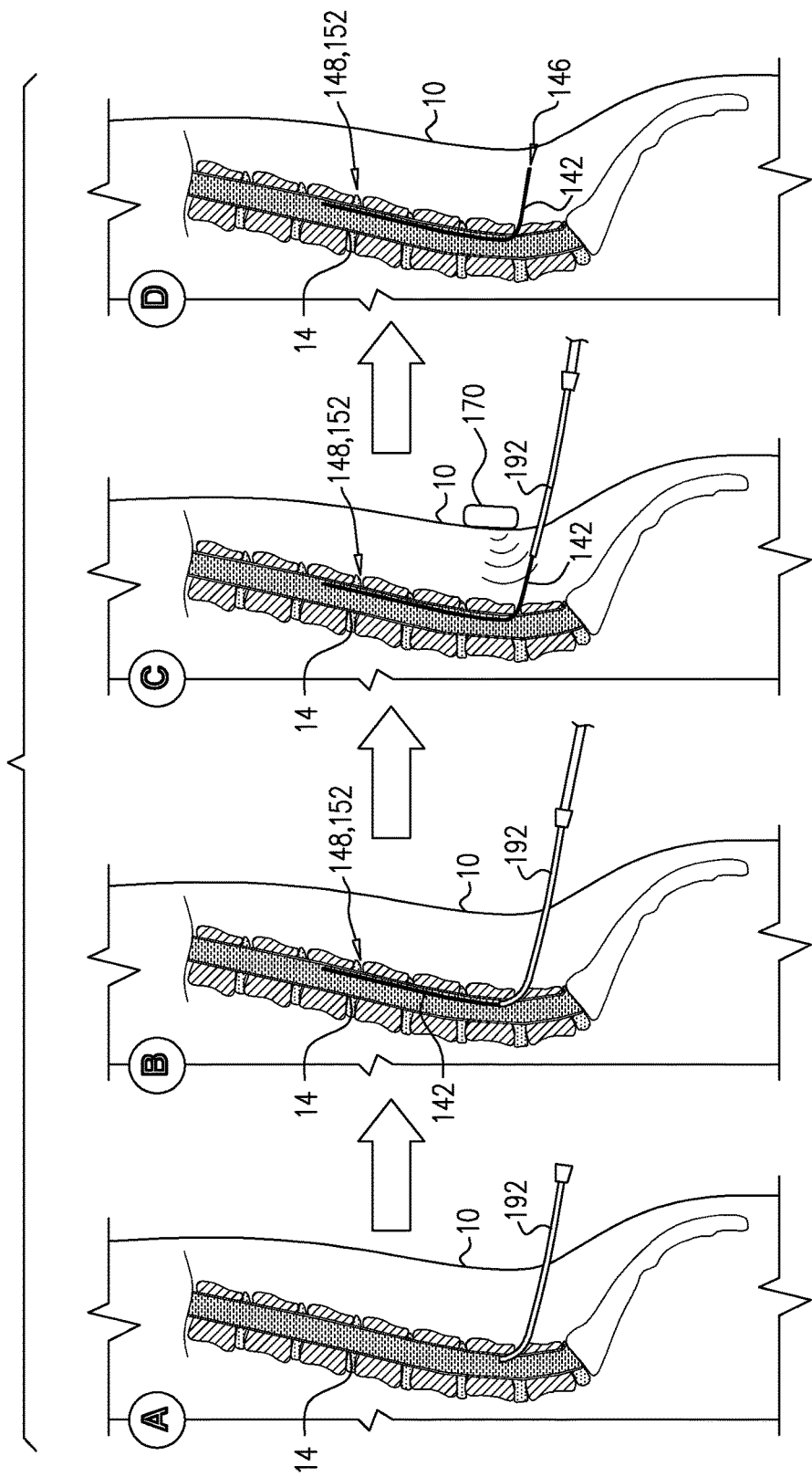

EXTRACORPOREAL IMPLANT CONTROLLERS

CROSS-REFERENCES TO RELATED APPLICATIONS

The present patent application is related to the following applications, filed on even date herewith:

(a) A U.S. patent application to Oron et al., filed on even date herewith, and entitled "Anchors and implant devices"; and (b) A U.S. patent application to Plotkin et al., filed on even date herewith, and entitled "Transmitting coils for neurostimulation".

All of the above-mentioned applications are assigned to the assignee of the present application and incorporated herein by reference.

FIELD OF THE INVENTION

Some applications of the present invention relate in general to medical devices. More specifically, some applications of the present invention relate to apparatus and methods for controlling implants.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Many neurological disorders cause pain.

Neurostimulation is a clinical tool used to treat various neurological disorders. This technique involves modulation of the nervous system by electrically activating fibers in the body.

SUMMARY OF THE INVENTION

For some applications of the invention, apparatus and techniques are described for wirelessly powering an implant using a first extracorporeal controller during the day, and a second extracorporeal controller during the night. Typically, the first controller is battery-powered, and the second controller is mains-powered, and differences between the controllers and their stimulation parameters reflect these different power supplies. For example, the battery-powered controller (i) is portable, (ii) is typically placed close to (e.g., on) the skin of the subject, and (iii) is typically placed directly over the implantation site of the implant, such that toe implant receives a relatively high proportion of the wireless bower transmitted by the battery-powered controller. In contrast, the mains-powered controller (i) is typically used while connected to mains power, (ii) is typically placed further from the skin of the subject, and (iii) provides power over a relatively large zone (allowing the subject to move with respect to the controller), such that the implant receives a relatively low proportion of the wireless power transmitted by the mains-powered controller. Typically, the mains-powered controller provides wireless power for a greater proportion of a given period (e.g., during a sleeping period) than does the battery-powered controller (e.g., during a wakeful period).

For some applications of the invention, apparatus and techniques are described for facilitating placement of an extracorporeal controller with respect to an implanted implant, so as to wirelessly power the implant using the controller.

For some applications of the invention, apparatus and techniques are described for implanting an electrode region of a rod-shaped implant within a spinal canal, and wirelessly powering the implant using an extracorporeal controller. For some applications, the controller has electrodes that are used for applying Transcutaneous Electrical Nerve Stimulation (TENS) in addition to wirelessly powering the implant. For applications, the controller one or more electromyographic (EMG) electrodes, a gyroscope, and/or an accelerometer, and the wireless powering of the implant is adjusted according to signals received from one or more of these elements.

There is therefore provided, in accordance with an application of the present invention, apparatus for treating a condition of a subject, the apparatus including:

a first controller, having a mass of 10-500 g and a volume of 25-250 cm^3, and including:
  at least, one first-controller antenna configured to transmit a first wireless power signal having a first signal power;
  a battery configured to store battery power;
  a first-controller control unit configured to use the battery power no drive the first-controller antenna to transmit the first wireless power signal; and
  a user input device, operable by the subject to power the first-controller control unit using the battery; and a second controller, including:
  at least one second-controller antenna, configured to transmit a second wireless power signal having a second signal power;
  a mains electricity connector; and
  a second-controller control unit, configured to use power from the mains electricity connector to drive the second-controller antenna to transmit the second wireless power signal; and an implant, configured to be implanted in tissue of the subject, the implant including:
  one or more tissue-contacting electrodes, configured to be placed in contact with the tissue;
  at least one implant antenna configured to receive 1-10 percent of the first signal power of the first wireless power signal, and to receive 0.01-1 percent of the second signal power of the second wireless power and
  circuitry configured (i) to be powered by the received 1-10 percent of the first signal power, and to responsively drive the one or more electrodes to apply a current, and (ii) to be powered by the received 0.01-1 percent of the second signal power, and to responsively drive the one or more electrodes to apply the current.

In an application, the battery is rechargeable, and the first controller is configured to recharge the battery by receiving the second wireless power signal.

In an application, the first controller is capable, on a single charge of the battery, to drive the first-controller antenna to transmit the first wireless power signal for a total wireless power transmission time that is less than 3 hours.

In an application, the implant does not include a non-transient power storage element.

In an application:
the implant includes a sensor,
the circuitry is configured to power the sensor responsively to the power received by the implant antenna,
the sensor is configured to, when powered by the circuitry responsively to the power received by the implant antenna, detect a factor related to the condition of the subject, and the circuitry is further configured to receive a signal from the sensor, and drive the one or more electrodes to apply the current at least in part responsively to the power received by the implant antenna, and at least in part responsively to the received signal.

In an application, the first controller is a hand-held controller.

In an application, the implant is injectable, and has a longitudinal axis and a cross-sectional area, transverse to the longitudinal axis, of 0.5-3 mm^2.

In an application, the implant is injectable, and the one or more tissue-contacting electrodes are configured to be placed in contact with the tissue by injection of the implant into the tissue.

In an application, the at least one second-controller antenna has an effective area of 400-2500 cm^2 and a thickness of 1-10 mm.

In an application, the first controller has a longest dimension of 6-15 cm.

In an application, the circuitry of the implant is configured, in response to receiving the first wireless power signal, to transmit a juxtaposition signal that includes information indicative of a juxtaposition between the implant and the first controller.

In an application, the apparatus is for use with a cellphone, and:
the at least one first-controller antenna includes a cellphone-interfacing antenna configured to communicate with the cellphone,
the juxtaposition signal is a first juxtaposition signal, and
the first controller is configured to receive the first juxtaposition signal, and to responsively drive the cellphone interfacing antenna to transmit a second juxtaposition signal that includes information indicative of the juxtaposition between the implant and the first controller, and (ii) is receivable by the cellphone.

In an application, the implant antenna is configured to receive the 1-10 percent of the first signal power while (i) the implant is implanted in the tissue, (ii) the first controller is disposed against skin of the subject directly superficially to the implant, and (iii) the first-controller control unit drives the first-controller antenna to transmit the first wireless power signal.

In an application, the implant antenna is configured to receive the 0.01-1 percent of the second signal power while (i) the implant is implanted in the tissue, (ii) the subject is lying on a bed in which the second controller is disposed, and (iii) the second-controller control unit drives the second-controller antenna to transmit the second wireless power signal.

In an application, the second-controller control unit has a longest period of power transmission with no user input, that is at least 1 hour.

In an application, the second-controller control unit has a longest period of power transmission with no user input, that is at least 2 hours.

In an application, the first-controller control unit has a longest period of power transmission with no user input, that is less than 1 hour.

In an application, the first-controller control unit has a longest period of power transmission with no user input, that is less than 10 min.

In an application, the first controller is incapable of powering the implant when a distance between the first-controller antenna and the implant antenna is greater than 10 cm.

In an application, the second controller is capable of powering the implant when a distance between the second-controller antenna and the implant antenna is greater than 20 cm.

In an application, the first-controller control unit is configured to configure the first wireless power signal such that the first signal power is 0.1-1 W.

In an application, the second-controller control unit is configured to configure the second wireless power signal such that the second signal power is 2-100 W.

In an application, the first controller and the second controller are configured to communicate therebetween information regarding a transmission of wireless power selected from the group consisting of: a transmission of the first wireless power signal, and a transmission of the second wireless power signal.

In an application, the second controller is configured to configure at least one transmission of the second wireless power signal responsively to receiving, from the first controller, information regarding at least one transmission of the first wireless power signal.

There is further provided, in accordance with an application of the present invention, a method for use with a subject that benefits from application of an electric current to a tissue site, the method including:
during a sleeping period in which the subject is sleeping, applying the current to the tissue site for a first proportion of the sleeping period; and
during a wakeful period in which the subject is awake, the wakeful period extending from the sleeping period to an immediately-subsequent sleeping period, applying the current to the tissue site for a second proportion of the wakeful period that is greater than zero and less than one-third of the first proportion,
and the wakeful period is a period during which the subject would benefit more from (a) applying the current to the tissue site for a third proportion of the wakeful period that is greater than two-thirds of the first proportion, than from (b) applying the current to the tissue site for the second proportion of the wakeful period.

There is further provided, in accordance with an application of the present invention, a method for use with a subject suffering from a condition that benefits from application of electric current to a tissue site, the method including:
during a sleeping period in which the subject is sleeping, applying a first amount of energy to the tissue site by applying electric current to the tissue site; and
during a wakeful period in which the subject is awake, applying a second amount of energy by applying electric current to the tissue site, the second amount of energy being greater than zero and less than one-third of the first amount of energy,
and the wakeful period (i) is defined as an entire period between the sleeping period and an immediately subsequent sleeping period, and (ii) is a period during which the condition would benefit more from applying a third amount of energy by applying electric current to the tissue site that is greater than two-thirds of the first amount of energy, than from applying the second amount of energy current to the tissue site by applying electric current.

There is further provided, in accordance with an application of the present invention, a method for use with an implant implanted in tissue of a subject, the method including:
during a sleeping period in which the subject is sleeping, wirelessly powering the implant to apply an electric current to the tissue by wirelessly transmitting power using a mains-powered controller while the mains-powered controller is connected to mains electricity; and during a wakeful period in which the subject is awake, wirelessly powering the implant to apply an electric current to the tissue by wirelessly transmitting power using a battery-powered controller while the battery-powered controller is powered by a battery and is not connected to mains electricity.

In an application, the step of wirelessly powering the implant during the wakeful period is performed by the subject operating the battery-powered controller.

There is further provided, in accordance with application of the present invention, apparatus including an implant, the implant including:

an injectable rod-shaped housing, having:
  a distal end and a proximal end,
  a distal portion that extends proximally from the distal end,
  a proximal portion that extends between the proximal and the distal portion, and is deflectable with respect to the distal portion, and
  a length from the distal end to the proximal end of 15-40 cm;
a plurality of implant electrodes distributed, on an outer surface of the housing, along an electrode region of the distal portion of the housing, the electrode region extending from a distal-most implant, electrode of the plurality of implant electrodes no a proximal-most implant electrode of the plurality of implant electrodes;
an implant antenna, configured to receive wireless power, and disposed within the proximal portion of the housing and at least 15 cm along the housing from the distal-most implant electrode; and
implant circuitry, disposed within the housing, and configured to use the received wireless power to drive one or more of the plurality of implant electrodes to apply a current.

In an application, the housing is injectable via an epidural needle.

In an application, the housing is injectable via a Tuohy needle.

In an application, the implant circuitry is disposed within the proximal portion of the housing.

In an application, a diameter of the housing, measured transverse to the length of the housing, is 1-3 mm.

In an application, the distal portion is flexible and the proximal portion is rigid.

In an application, the housing has a uniform cross-sectional shape along the length of the housing.

In an application, the implant does not include a battery.

In an application, the apparatus further includes an extracorporeal controller, including:
  a battery configured to store battery power;
  a controller antenna;
  controller circuitry configured to use the battery power to drive the controller antenna to transmit the wireless power; and
  a housing that houses the battery, the controller antenna, and the controller circuitry.

In an application, the extracorporeal controller has a concave skin-facing face, shaped to receive a body portion of a subject in which the implant has been implanted.

In an application, the concave skin-facing face defines a concavity having a radius of curvature of 5-8 cm.

In an application, the apparatus further includes a mounting member, configured to facilitate mounting of the housing on a subject extracorporeally over the proximal portion of the housing.

In an application, the mounting member includes a belt configured to extend around a torso of the subject.

In an application, the extracorporeal controller further includes one or more controller electrodes disposed on a skin-facing face of the housing, and the mounting member is configured to facilitate mounting of the housing such that the controller electrodes are disposed against skin of the subject.

In an application, the extracorporeal controller further includes one or more controller electrodes disposed on a skin-facing face of the housing, and the housing is configured to be mounted on a subject extracorporeally over the proximal portion of the housing, such that the controller electrodes are disposed against skin of the subject.

In an application, the electrode region of the implant is configured to be placed within 5 mm of a spinal nerve of the subject, and the housing is configured, to be mounted to the subject such that at least one of the controller electrodes is disposed on a skin site that is directly superficial to at least one muscle of a myotome not served by the spinal nerve.

In an application, (i) the controller antenna is disposed with respect to the at least one controller electrode, and (ii) the controller antenna, the controller circuitry, the implant antenna, and the implant circuitry are configured, such that when the controller electrodes are disposed on the skin site, and the electrode region is disposed within 5 mm of the spinal nerve, the implant circuitry is powerable by the wireless power.

In an application, the electrode region of the implant is configured to be placed within 5 mm of a spinal nerve of the subject, and the housing is configured to be mounted to the subject such that at least one of the controller electrodes is disposed on a skin site that is directly superficial to at least one muscle of a myotome served by the spinal nerve.

In an application, (i) the controller antenna is disposed with respect to the at least one controller electrode, and (ii) the controller antenna, the controller circuitry, the implant antenna, and the implant circuitry are configured, such that when the controller electrodes are disposed on the skin site, and the electrode region is disposed within 5 mm of the spinal nerve, the implant circuitry is powerable by the wireless power.

In an application, the electrode region of the implant is configured to be placed within 5 mm of a spinal nerve of the subject, and the housing is configured to be mounted to the subject such that at least one of the controller electrodes is disposed on a skin site within a dermatome not served by the spinal nerve.

In an application, (i) the controller antenna is disposed with respect to the at least one controller electrode, and (ii) the controller antenna, the controller circuitry, the implant antenna, and the implant circuitry are configured, such that when the controller electrodes are disposed on the skin site, and the electrode region is disposed within 5 mm of the spinal nerve, the implant circuitry is powerable by the wireless power.

In an application, the electrode region of the implant is configured to be placed within 5 mm of a spinal nerve of the subject, and the housing is configured to be mounted to the subject such that at least one of the controller electrodes is disposed on a skin site within a dermatome served by the spinal nerve.

In an application, (i) the controller antenna is disposed with respect to the at least one controller electrode, and (ii) the controller antenna, the controller circuitry, the implant antenna, and the implant circuitry are configured, such that when the controller electrodes are disposed on the skin site, and the electrode region is disposed within 5 mm of the spinal nerve, the implant circuitry is powerable by the wireless power.

In an application, the controller electrodes include electromyographic electrodes, and the controller circuitry is configured to receive an electromyographic signal from the electromyographic electrodes, and to drive the controller antenna to transmit the wireless power at least in part responsively to the received electromyographic signal.

In an application, the controller circuitry is configured to identify, using the electromyographic signal, a muscle activity indicative of spasm and to drive the controller antenna to transmit the wireless power at least in part responsively to the identification.

In an application, the controller circuitry is configured identify, using the electromyographic signal, a muscle activity indicative of pain and to drive the controller antenna to transmit the wireless power at least in part responsively to the identification.

In an application, the controller circuitry is configured to identify walking, using the electromyographic signal, and to inhibit transmission, of the wireless power in response to the identification.

In an application, the controller further includes a motion sensor, and the controller circuitry is configured:
to receive a motion signal from the motion sensor, and
to inhibit transmission of the wireless power in response to the motion sensor detecting a motion.

In an application, the controller circuitry is configured to inhibit transmission of the wireless power in response to the motion sensor detecting a motion indicative of walking.

In an application, the controller circuitry is configured to drive the electrodes to apply a pain-relieving current to the skin.

In an application, the controller circuitry is configured to drive the electrodes to apply the pain-relieving current generally at the same time as driving the controller antenna to transmit the wireless power.

In an application, the controller circuitry is configured to receive an electromyographic signal from the electrodes, and to drive the controller antenna to transmit the wireless power at least in part responsively to the received electromyographic signal.

In an application, the controller circuitry is configured to identify, using the electromyographic signal, a muscle activity indicative of spasm and to drive the controller electrodes to apply the pain-relieving current at least in part responsively to the identification.

In an application, the controller circuitry is configured to identify, using the electromyographic signal, a muscle activity indicative of pain and to drive the controller electrodes to apply the pain-relieving current at least in part responsively to the identification.

In an application, the controller circuitry is configured to identify, using the electromyographic signal, a muscle activity indicative of walking, and to inhibit transmission of the wireless power in response to the identification.

In an application, the controller circuitry is configured identify, using the electromyographic signal, a muscle activity indicative of bending, and to inhibit transmission of the wireless power in response to the identification.

In an application, the controller further includes a motion sensor, and the controller circuitry is configured:
to receive a motion signal from the motion sensor, and
to inhibit transmission of the wireless power in response to the motion sensor detecting a motion.

In an application, the distal portion of the housing is dimensioned to be advanced distally through a spinal entry point of a spinal column of a subject and into the spinal column.

In an application, the distal portion of the housing is dimensioned to be advanced distally through an intervertebral foramen of a subject alongside a spinal nerve of the subject, and into a spinal canal of the subject such that the electrode region is disposed in the spinal canal.

In an application, the distal portion of the housing is dimensioned to be advanced distally into an epidural space of the spinal column of the subject such that the electrode region is disposed in the epidural space.

In an application, the housing is dimensioned and shaped such that while the electrode region is disposed in the epidural space, the proximal portion is positionable at an angle of 30-60 degrees with respect, to the distal portion, such that the proximal portion extends superficially at least in part, from the spinal entry point.

In an application, the housing is dimensioned and shaped such that while the electrode region is disposed in the epidural space, the proximal portion is positionable such that the proximal portion extends caudally at least in part, from the spinal entry point.

In an application, the plurality of implant electrodes includes 4-8 electrodes.

In an application, the plurality of implant electrodes includes exactly 4 electrodes.

In an application, the plurality of implant electrodes includes exactly 8 electrodes.

There is further provided, in accordance with an application of the present invention, apparatus, for use with a consumer device that includes a display, including:
an implant including:
one or more tissue-contacting electrodes;
at least one implant antenna configured to receive wireless power; and
implant circuitry configured to use the received wireless power to drive the one or more electrodes to apply a current; and
a hand-held controller, having a mass of 10-500 g and a volume of 25-250 cm^3, and including:
one or more controller antennas, at least one of the controller antennas configured to transmit the wireless power, and at least, one of the controller antennas configured to communicate with the consumer device;
a battery configured to store battery power; and
controller circuitry configured to:
use the battery power to drive at least, one of the controller antennas to transmit the wireless power,
to identify a position of the controller with respect to the implant, and
to drive at least one of the controller antennas to transmit juxtaposition information to the consumer device about the position of the controller with respect to the implant.

In an application, the consumer device is a cellphone.

In an application, the one or more controller antennas include bifunctional antenna configured to transmit the wireless power and to communicate with the consumer device.

In an application, the one or more controller antennas include a first controller antenna configured to communicate with the consumer device, and a second controller antenna configured to transmit the wireless power, and not configured to communicate with the consumer device.

In an application:

the implant circuitry is configured:
to detect a juxtaposition of the controller with respect to the implant, at least in part responsively to the wireless power received by the at least one implant antenna, and
to transmit a signal including information about the juxtaposition, and
the controller is configured to receive the signal, and the controller circuitry is configured to identify the position of the controller with respect to the implant, at least in part responsively to the received signal.

In an application, the controller is configured to transmit the juxtaposition information to the consumer device independently of a cellular network.

In an application, the controller is configured to transmit the juxtaposition information to the consumer device via a Bluetooth connection.

In an application, the controller is configured to transmit the juxtaposition information to the consumer device via a Near Field Communication connection.

In an application, the controller is configured to transmit the juxtaposition information to the consumer device via a WiFi connection.

There is further provided, in accordance with an application of the present invention, apparatus for use with an implant implantable in tissue of a subject, the implant including an implant antenna, the apparatus including a controller, the controller including:
a housing, placeable on skin of the subject such that a skin-facing face of the housing faces the skin;
at least one controller antenna disposed within the housing;
one or more controller electrodes disposed on a skin-facing face of the housing such that the placement of the housing on the skin places the one or more electrodes in contact with the skin;
a battery configured to store battery power; and
controller circuitry:
powered by the battery,
in electrical communication with the controller electrodes, and
configured to use the battery power to drive the controller antenna to transmit wireless power that is receivable by the implant antenna.

In an application, the controller circuitry is configured to use the battery power to drive the one or more electrodes to apply a current to the skin.

In an application, the controller circuitry is configured to change a temperature of at least a portion of the skin facing face of the housing.

In an application, the controller circuitry is configured to reduce the temperature of at least the portion of the skin-facing face of the housing.

In an application, the controller circuitry is configured to increase the temperature of at least the portion of the skin-facing face of the housing.

In an application, the controller is configured to detect a motion of the subject, and to inhibit driving of the controller antenna in response to detection of the motion.

In an application, the controller includes a motion sensor that is configured to detect the motion.

In an application, the one or more controller electrodes include one or more electromyographic electrodes, and the controller circuitry is configured to detect the motion by receiving an electromyoqraphic signal that is indicative of the motion.

In an application, the controller circuitry is configured to use the battery power to drive at least one of the one or more electrodes to apply a treatment current to the skin.

In an application, the one or more controller electrodes include one or more electromyographic electrodes, and the controller circuitry IS configured to receive electromyographic signal from the electromyographic electrodes, and to responsively transmit the wireless power.

In an application, the controller circuitry is configured to, responsively to receiving the electromyographic signal from the electromyographic electrodes, drive the at least one of the electrodes to apply the treatment current to the skin.

In an application, the one or more controller electrodes include one or more EMG electrodes, and the controller circuitry is configured to receive an EMG signal from the EMG electrodes.

In an application, the controller circuitry is configured to drive the controller antenna at least in part responsively to the received EMG In an application, the apparatus further includes the implant, and the implant includes:
one or more implant electrodes disposed on an outer surface of the implant; and
implant circuitry configured to use the power received by the implant antenna to drive the implant electrodes to apply a current to the tissue.

The present invention will be more fully understood from the following detailed description of applications thereof, taken together with the drawings, in which:

BRIEF DESCRIPTION OF THE DRAWINGS

FIGS. 1A-B and 2 are schematic illustrations of a system, and use thereof, for treating a condition of a subject, in accordance with some applications of the invention;

FIGS. 5A-C and 6 are schematic illustrations of a system, and use thereof, for treating a condition of a subject, in accordance with some applications of the invention.

DETAILED DESCRIPTION OF EMBODIMENTS

Figure 2:
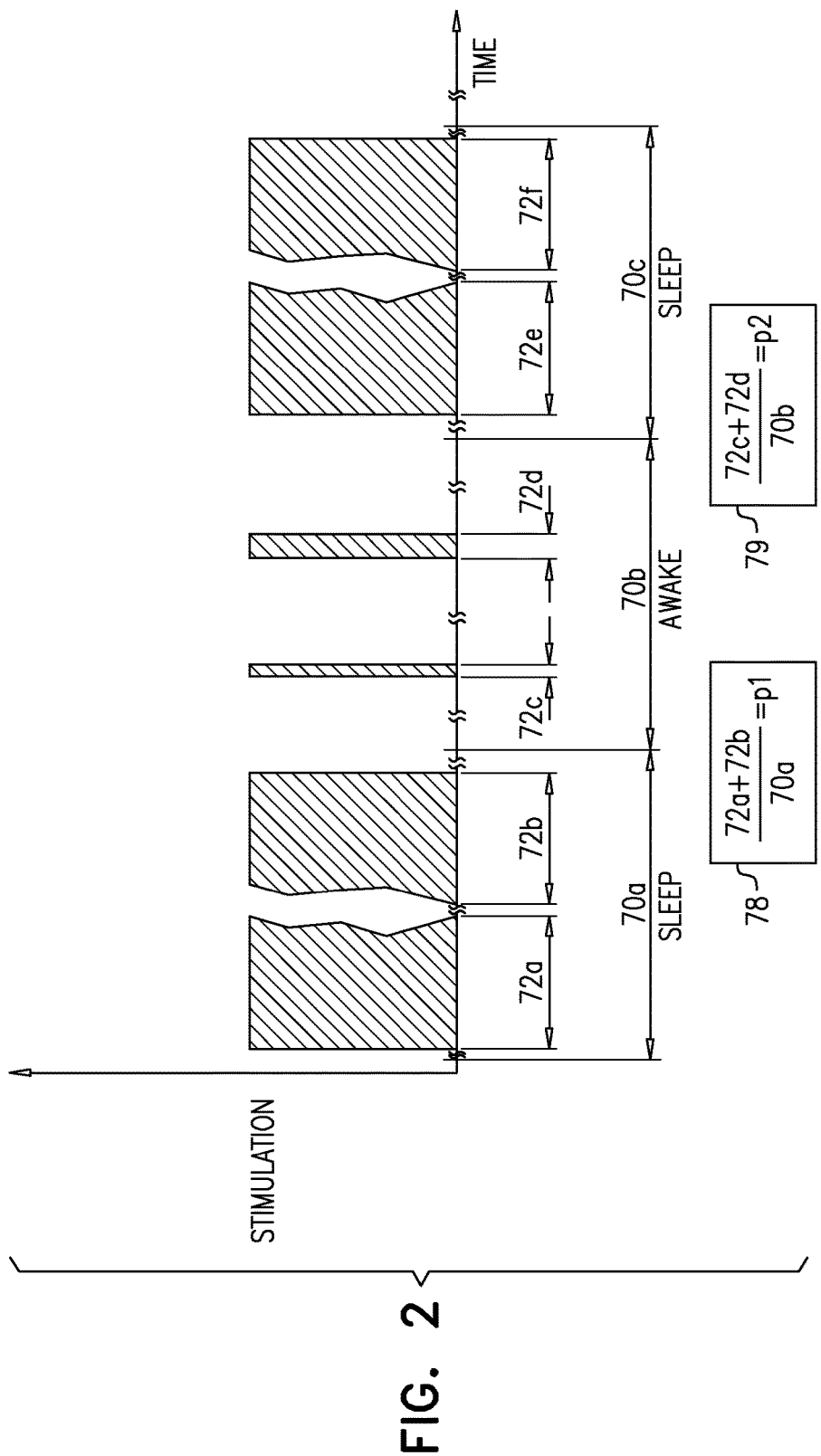

Reference is made to FIGS. 1A-B and 2, which are schematic illustrations of a system 20, and use thereof, for treating a condition of a subject 10, in accordance with some applications of the invention. System 20 comprises an implant 30, a first extracorporeal controller 40, and a second extracorporeal controller 50.

Implant 30 comprises one or more tissue-contacting electrodes 32, an antenna 34 configured to receive wireless power, and circuitry 35 configured to be powered by the wireless power received by antenna 34, and to responsively drive the electrodes to apply a treatment current to tissue that is in contact with the electrodes (e.g., circuitry 35 defines and/or comprises a control unit 36). Typically, implant 30 does not comprise a battery or other non-transient power storage element, advantageously reducing the size of the implant. (However implant 30 may comprise a capacitor.) The current is configured, and the implant is positioned, to treat the condition of the subject, such as by neuromodulation. For some applications implant 30 is injectable, such that injection of the implant into tissue places electrodes 32 in contact with the tissue. For example, implant 30 may have a transverse cross-sectional area (i.e., transverse to the longitudinal axis of the implant along which the implant is injected) of 0.5-3 mm^2 (e.g., 0.5-2 mm^2).

First controller 40 is portable. For example, controller 40 may have a mass of greater than 10 g and/or less than 500 g (e.g., 10-500 g), and/or a volume of greater than 25 cm^3 and/or less than 250 cm^3 (e.g., 25-250 cm^3). Alternatively or additionally, controller 40 may have a longest dimension of 6-15 cm. For some applications controller 40 is configured to be hand-held. Alternatively or additionally, controller 40 may be configured to be coupled to the subject being treated. Controller 40 comprises a battery 42, at least one antenna 44, and a control unit 46 configured to use power from the battery to drive antenna 44 to transmit wireless power (i.e., a wireless power signal). Controller 40 typically further comprises a user input device 48, such as a switch or button, that is operable by the subject to power control unit 46 using battery 42.

Second controller 50 comprises a mains electricity connector 52, at least one antenna 54, and a control unit 56 configured to use power from the mains connector (e.g., while the control unit is connected to mains electricity) to drive antenna 54 to transmit wireless power (i.e., a wireless power signal). Controller 40 typically further comprises a user input device, such as a switch or button, that is operable by the subject to power control unit 46 using battery 42. Controller 50 is typically not portable, e.g., due to its dependence on mains electricity and/or due to its size. Antenna 54 is typically housed in a housing 58, and the housing and antenna are dimensioned, to be placed close to the subject's bed. 12 (e.g., in or under the mattress, as shown).

Antenna 34 of implant 30 is configured to receive and be powered by wireless power both from controller 40 and from controller 50. In general, and as described hereinbelow, system 20 is configured such that implant 30 is (i) powered by controller 50 while the subject is in bed (e.g., during a sleeping period), and (ii) powered by controller 40 while the subject is not in bed, e.g., during the day.

Controller 40 typically powers the implant while antenna is less than 5 cm (e.g., 3 cm) from implant 30 (e.g., because the controller is typically disposed against the part of the subject in which the implant is located), and is generally stationary with respect to the implant during use in contrast, controller 50 typically powers the implant while antenna 54 is at least 5 cm (e.g., at least 25 cm) from implant 30, e.g., due to the thickness of the mattress and the distance between the implant and the mattress. Additionally, during the sleeping period the subject (and thereby the implant) typically moves with respect to antenna 54. Antenna 54 therefore has an effective area d4 that is greater (e.g., 4 times greater, such as at least 8 times greater) than that of antenna 44 of controller 40. For example, antenna 54 may have an effective area d4 of 400-2500 cm^2, and a thickness of 1-10 mm. The relatively large effective area of antenna 54 allows implant 30 to be reliably wirelessly powered while the subject is sleeping, despite distance and movement. It is to be noted that controllers 40 and 50, which are each shown as comprising a single antenna, may each comprise a plurality of antennas, and thereby the described effective area of antenna 44 and antenna 54 may instead be the effective area of the respective plurality of antennas.

Due to the nature of controller 50 and its use, controller 50 typically transmits more wireless power in order to power implant 30, than does controller 40. That is, the proportion of the power transmitted by antenna 44 that is received by antenna. 34 when implant 30 is powered by controller 40, is greater than the proportion of the power transmitted by antenna 54 that is received by antenna 34 when implant 30 is powered by controller 50 (e.g., at least 10 times greater, e.g., at least 100 times greater, such as at least 1.000 times greater). For example, whereas when implant is powered by controller 40 (e.g., when controller 40 is disposed against the subject, and/or antenna 34 is disposed 0.1-10 cm from antenna 44) antenna 34 typically receives 1-10 percent of the power transmitted by antenna 44 (e.g., 1-3 percent or 3-10 percent), when implant 30 is powered by controller 50 (e.g., when the subject is in bed, and/or antenna 34 is disposed 1-50 cm from antenna 54) antenna 34 typically receives 0.01-1 percent of the power transmitted by antenna 54 (e.g., 0.01-0.1 percent or 0.1-1 percent).

For some applications, controller 50 transmits wireless power at a wattage that is 5-100 times that transmitted by controller 40. For some applications, controller 50 transmits 2-100 W of wireless power, and controller 40 transmits 0.1-1 W oil wireless power.

Typically, controller 50 is configured to transmit power with no user input for at least 1 hour (e.g., at least 2 hours, such as at least 4 hours). That is, controller 50 has a longest period of power transmission with no user input, that is at least 1 hour (e.g., at least 2 hours, such as at least 4 hours). Controller 50 typically powers implant 30 frequently and/or continuously during a sleeping period (e.g., in the absence of input from the subject and/or without the knowledge of the subject), e.g., providing frequent and/or continuous treatment and/or prophylaxis. Conversely, for some applications controller 40 has a longest, period of power transmission with no user input, that is less than 1 hour (e.g., less than 10 min, as less than 5 min). For example, controller 40 may only transmit power while user input device 48 is operated, or may transmit power for only 5 or 10 min after operation of device 48.

Controller 40 is typically used to power implant 30 when the subject is awake and operates device 48, e.g., in response to noticing symptoms of the condition. For example, implant 30 may be implanted close to the vagal nerve (e.g., a within 5 mm of the vagal nerve) of the subject so as to treat epilepsy (e.g., as shown in FIG. 1A), and in response to noticing signs of the onset of an epileptic seizure, the subject may activate controller 40 by operating device 48. (For applications of the invention in which controller 40 is hand-held, rather than secured to the neck of the subject, the subject would also place the controller against the part of the subject in which the implant is located, e.g., against the neck.)

For some applications, on a single charge of battery 42, controller 40 is capable of a total wireless power transmission time of less than 3 hours (e.g., less than 1 hour and/or more than 5 min, such as 5-15 min). For some applications, on a single charge of battery 42, controller 40 is capable of a continuous power transmission time of less than 1 hour and/or more than 5 min (e.g., 5-15 min) (e.g., duration 72c and/or duration 72d, described hereinbelow with reference to FIG. 2, are each less than 1 hour and/or more than 5 min, such as 5-15 min). In contrast, controller 50, which is powered by mains electricity, does not have this limitation.

For some applications, controller 40 is incapable of powering implant 30 when a distance between antenna 44 and antenna 34 is greater than 10 cm and/or greater than a diameter do of antenna 44. In contrast, controller 50 is typically capable of powering implant 30 when a distance between antenna 54 and antenna 34 is greater than 20 cm (e.g., between 20 and 50 cm). For some applications, controller 50 is also incapable of powering implant 30 when the distance between antenna 54 and antenna 34 is greater than a diameter of antenna 54, and the increased operational distance at which controller 50 is capable of powering the implant is due to the increased size of antenna 54 compared to antenna 44.

FIG. 2 shows example of a wakeful period 70b immediately following a sleeping period 70a, and immediately preceding another sleeping period 70c. For example, FIG. 2 may represent a day between two nights. During sleeping period 70a, controller 50 powers implant 30 to apply current for two durations 72a and 72b, the sum of the durations being a proportion p1 of sleeping period 70a (see equation in box 78). During wakeful period 70b, controller 40 is occasionally used to power implant 30 to apply current. In the example shown in FIG. 2, controller 40 is used to power implant 30 to apply current during a first duration 72c, and during a second duration 72d. The sum of the durations of the applications of current during period 70b is a proportion p2 of period 70b (see equation in box 79). In a wakeful period in which at least current application, is applied, proportion p2 is typically greater than zero and less than one-third of proportion p1.

It is to noted that the example of two current applications during period 70a, and two current applications during period 70b, is purely illustrative, and not intended to be limiting.

For some applications, proportion p2 is greater than zero and less than one-third of proportion p1 even in cases in which the subject would benefit more if proportion p2 were greater this, such as more than two-thirds of proportion p1. Similarly, for some applications, the total amount of energy applied by the implant in the current applied during period 70b is greater than zero and less than one-third of the total amount of energy applied by the implant in the current applied during period 70a, even in cases in which the subject would benefit more if the total amount of energy applied during period 70b were greater this, such as more than two-thirds of the total amount of energy applied by the implant in the current applied during period 70a.

For some applications, a strength of the treatment current applied by implant 30 is higher when the implant is powered by controller 50 than when the implant is powered by controller 40. For some applications, the higher strength is due to the treatment current being applied at a greater (i.e., higher percentage) duty cycle. For some applications, the higher strength is due to the treatment current having a greater amplitude. For some applications, implant 30 applies the current of higher strength at least in part responsively to receiving wireless, power of higher strength from controller (optionally without identifying that the wireless power is received from controller 50 rather than controller 40). For some applications, implant 30 applies the current of higher strength at least in part responsively to receiving a signal from controller 50, e.g., the wireless power signal having a particular transmission pattern, a signal modulated onto the wireless power signal, or a separate wireless signal.

Because of the above-described differences between controllers 40 and 50 with regard to (i) portability, (ii) wireless power reception efficiency, (iii) duration of transmission in the absence of user input, (iv) proportion, of sleeping/ wakeful period during which power is transmitted, and (v) treatment current strength, controller 40 benefits from being powered by battery 42, whereas controller 50 benefits from being powered by mains electricity (via connector 52).

For some applications, controller 40 is configured to receive wireless power from controller 50 (e.g., via antenna 44, or via another antenna, not shown), and to recharge battery 42 using this received power. For example, controller 40 may be placed on or near the mattress while the subject is in bed. For some applications, controllers 40 and 50 may be configured to interface and communicate (e.g., wirelessly). For example, controller 50 may adjust a treatment scheduled for a subsequent sleeping period based on the treatment (s) applied during the preceding wakeful period, may compile a collated log of treatments, and/or may transmit the collated log a service provider (e.g., via a standard internet connection).

Reference is again made to FIGS. 1A-2. For some applications, implant 30 comprises a sensor 38, configured to detect a factor related to a condition of the subject; typically the condition being treated by system 20. Because implant 30 typically does not comprise a non-transient power source, sensor 38 is typically inactive until wireless power is received by the implant. Typically, sensor 38 provides a gate functionality, such that even if wireless power is received by antenna 24, control unit 36 only drives electrodes to apply the current when the detected factor (e.g., detected values of the factor) meet certain criteria (e.g., fall within a predetermined range). That is, sensor 38 drives electrodes 32 to apply the current only when (1) power is received from at least one of the controllers, and (2) a particular signal is received from the sensor. Such gate functionality may prevent unnecessary application, of current, that may otherwise be initiated by the subject's use of controller 40.

Figure 3A:
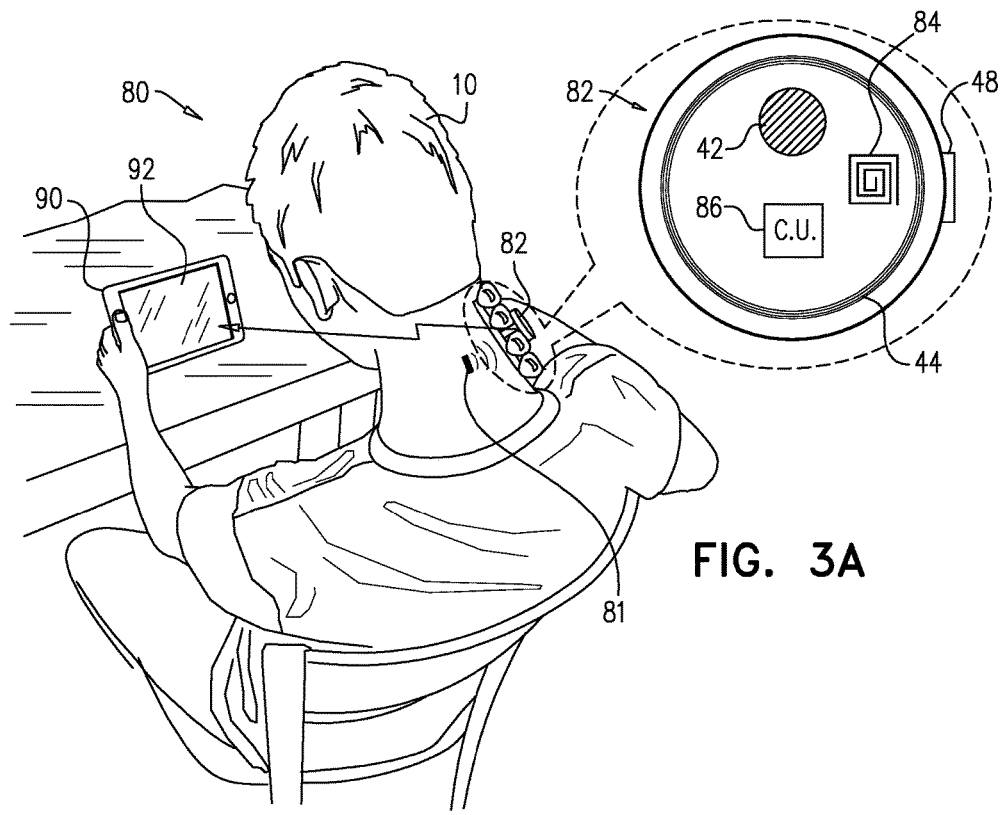
FIGS. 3A-C are schematic illustrations of a system, and use thereof, for treating a condition of a subject, in accordance with some applications of the invention.
Figure 3B:
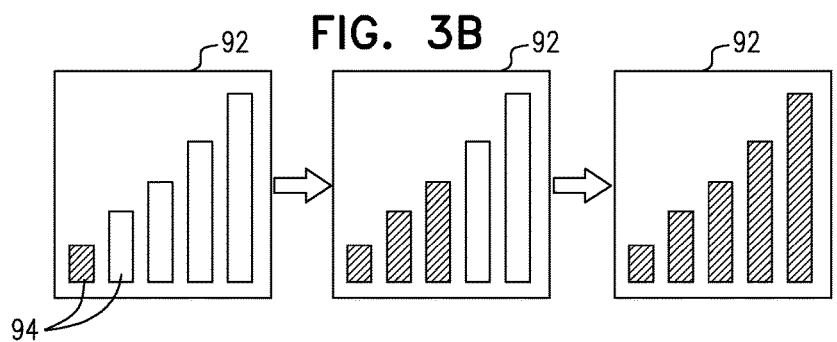
Figure 3C:
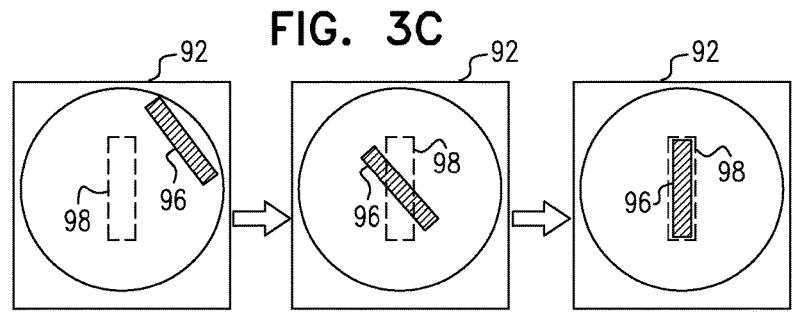

Reference is made to FIGS. 3A-C, which are schematic illustrations of a system 80, and use thereof, for treating a condition of a subject 10, in accordance with some applications of the invention. System. 80 comprises an implant 81, and a controller 82. For some applications implant 81 is identical to implant 30 (described hereinabove) except where noted. For some applications, controller 82 is identical to controller 40 (described hereinabove) except where noted. In addition to battery 42 and antenna 44, controller 82 comprises a cellphone-interfacing antenna 84 configured to facilitate communication between communicate with a cellphone 90 (or other similar ubiquitous consumer device having a display 92, such as a tablet computer), typically independently of a cellular network. For example, antenna 84 may facilitate communication between controller 82 (e.g., a control unit 86 thereof) and the cellphone via a Bluetooth connection, a Near Field Communication (NFC) connection, a WiFi connection, or another connection that is commonly supported by cellphones. For some applications controller 82 comprises a bifunctional antenna (e.g., antenna 174 is a bifunctional antenna and the controller does not comprise antenna 84) that is configured to transmit the wireless power to implant 81 and to communicate with cellphone 90.

System 80 is configured to detect a position (e.g., a translational and/or a rotational position) of controller 82 with respect to implant 81, and control unit 86 is configured to drive antenna 84 to transmit, to cellphone 90, juxtaposition information about the position of the controller with respect to the implant. Software on the cellphone (e.g., a downloadable application) provides a representation of the juxtaposition information, such that the subject may correctly position controller 82 for optimal transmission efficiency 20. FIGS. 3B-C are illustrative (but not limiting) examples of such representations. The respective first frame of each of FIGS. 3B-C indicates that controller 82 is not optimally positioned. The respective second frame of each of FIGS. 3B-C indicates improved positioning, and the respective third frame indicates optimal positioning.

FIG. 3B shows a representation that indicates signal strength using "bars" 94, which are already familiar to cellphone users with respect to cellular reception. FIG. 3C shows a representation of the actual position (e.g., translational and rotational position) of controller 82 with respect to implant 81, the representation including a representation 96 of the implant and a representation 98 of the optimal translational and rotational, position of the controller with respect to the implant. In the first frame representation 96 is translationally and rotationally offset with respect to representation 98. In the second frame representation 96 is translationally aligned, but rotationally offset, with respect to representation 98, typically indicating that controller 82 is disposed directly over implant 81, but should still be rotated to achieve optimal power reception. The third frame indicates that controller 82 is in the optimal position for implant 81 to receive power from controller 82.

For some applications, the detection of the juxtaposition between controller 82 and implant 81 is performed by the implant (e.g., in response to receiving at least a threshold amount of power from the controller), which transmits to the controller a signal including information indicative of the juxtaposition, and the controller is configured to receive the signal and to subsequently transmit the juxtaposition information to cellphone 90. This configuration is hypothesized to (a) reduce the signal strength required to be transmitted by implant 81 (e.g., the signal strength transmitted by the controller to the cellphone is higher than that transmitted by the implant to the controller), and/or (b) facilitate miniaturization of the implant (e.g., the hardware required to transmit the signal to be received by the cellphone may be larger than that required to transmit the signal to be received by the controller). For some applications implant 81 simply detects the overall strength of the received wireless power signal, and transmits this information, which may then be represented as shown in FIG. 3B. For some applications implant 81 also detects rotational juxtaposition, and transmits this information, which may then be represented as shown in FIG. 3C.

For some applications, at least partly responsively to juxtaposition information, controller 82 automatically stops transmitting wireless power (e.g., switches off), so as conserve power. For example, controller 82 may stop transmitting wireless power after a duration of the controller being not in proximity of implant 81 (e.g., subsequent to powering the implant, or simply when in a bag or pocket of the subject). Typically, such a duration is less than 1 min (e.g., 5-60 s, such as 10-30 s). Alternatively or additionally, controller 82 may provide an alert (e.g., an alarm) if the position of the controller is such that implant 81 is not sufficiently powered.

Figure 4A:
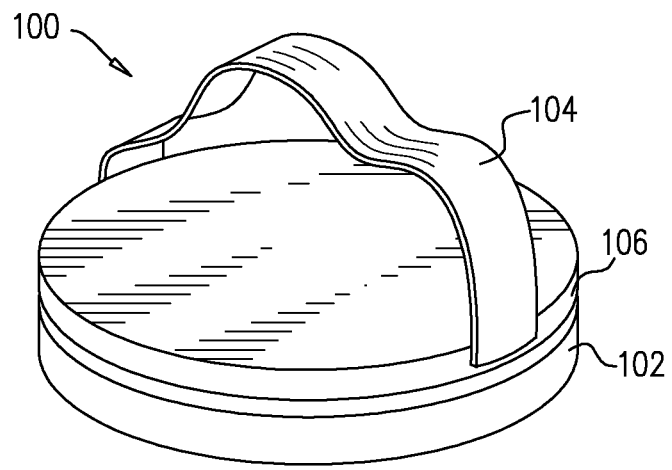
FIGS. 4A-D are schematic illustrations of hand-held controllers, in accordance with some applications of the invention.
Figure 4B:
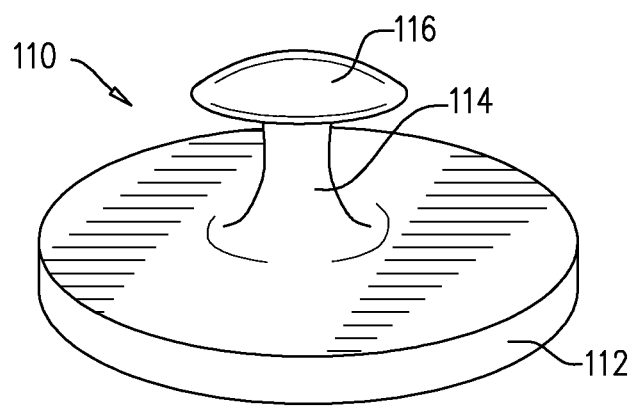
Figure 4C:
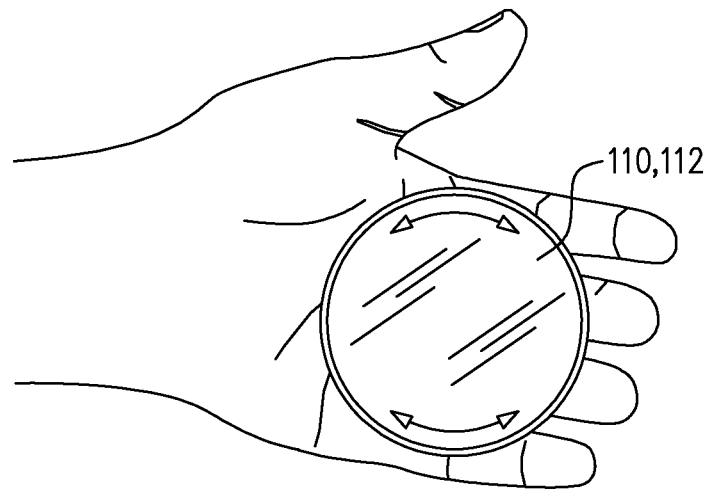

Reference is made to FIGS. 4A-D, which are schematic illustrations of hand-held controllers, in accordance with some applications of the invention. For some applications, FIGS. 4A-D represent embodiments of other controllers described herein, such as controller 40 and controller 82, mutatis mutandis. FIG. 4A shows a controller 100, which comprises a housing 102 and a hand-coupling member such as a strap 104. FIG. 4B shows a controller 110, which comprises a housing 112 and a hand-coupling member such as a shaft 114 (e.g., having a flange 116 at the top). Strap 104 fits around one or more fingers of the user (typically the subject being treated), whereas shaft 114 fits between two fingers of the subject. Both strap 104 and shaft 114 facilitate holding of the housing of the controller in the palm, of the hand, e.g., as shown in FIG. 4C (for controller 110, FIG. 3A also illustrates such holding, mutatis mutandis). For some applications, the hand-coupling member facilitates rotation of the housing with respect to the hand of the subject, e.g., as shown in FIG. 4C. For example, shaft 114 may simply be rotated while disposed between the fingers, and strap 104 may be rotatably coupled to housing 102 (e.g., by being coupled to a mount 106 that is rotatably coupled to the housing). For some such applications, the housing is rotatable using only the thumb and forefinger of the hand to which the controller is coupled.

Figure 4D:
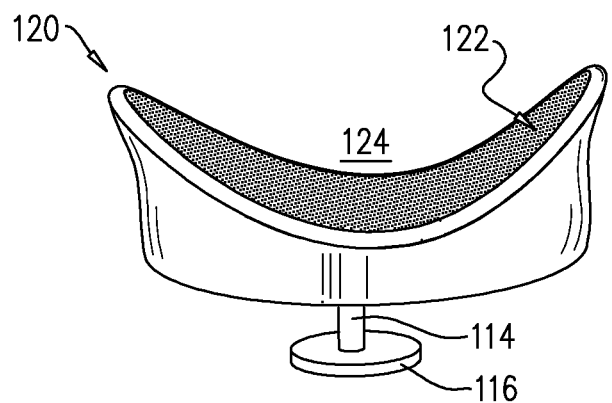

Controllers 40, 82, 100, and 110 each have a skin-facing (e.g., a skin-contacting face), and are typically configured to transmit the wireless power is the skin-facing face. For some applications, the skin-facing face of one or more of the controllers described herein defines a concavity that is shaped to generally receive (e.g., mate with) the part of the body of the subject in which the implant being controlled is disposed. For example, when the implant is disposed within the neck of the subject (e.g., as shown in FIGS. 1A and 3A), the concavity may be shaped to receive the neck of the subject, and may have a radius of curvature of 5-8 cm. FIG. 4D shows an example of such a concavity 124, defined by the skin-facing face 122 of a controller 120. For some applications, the concavity is aligned (e.g., rotationally aligned) with the controller's antenna such that placing the controller on the body part of the subject such that the concavity receives the body part optimally aligns the antenna with the antenna of the implant. For some applications, the controller and implant are configured to reduce the effect of rotational alignment on the efficiency of power transfer. For some such applications this is achieved using, mutatis mutandis, techniques described in a U.S. patent application to Plotkin et al. entitled "Transmitting coils for neurostimulation", filed on even date herewith.

Although the portable controllers described herein are generally described as being hand-held, it is to be noted that such controllers may additionally or alternatively be coupled to the subject (e.g., worn, such as by being strapped to the subject).

Figure 5B:
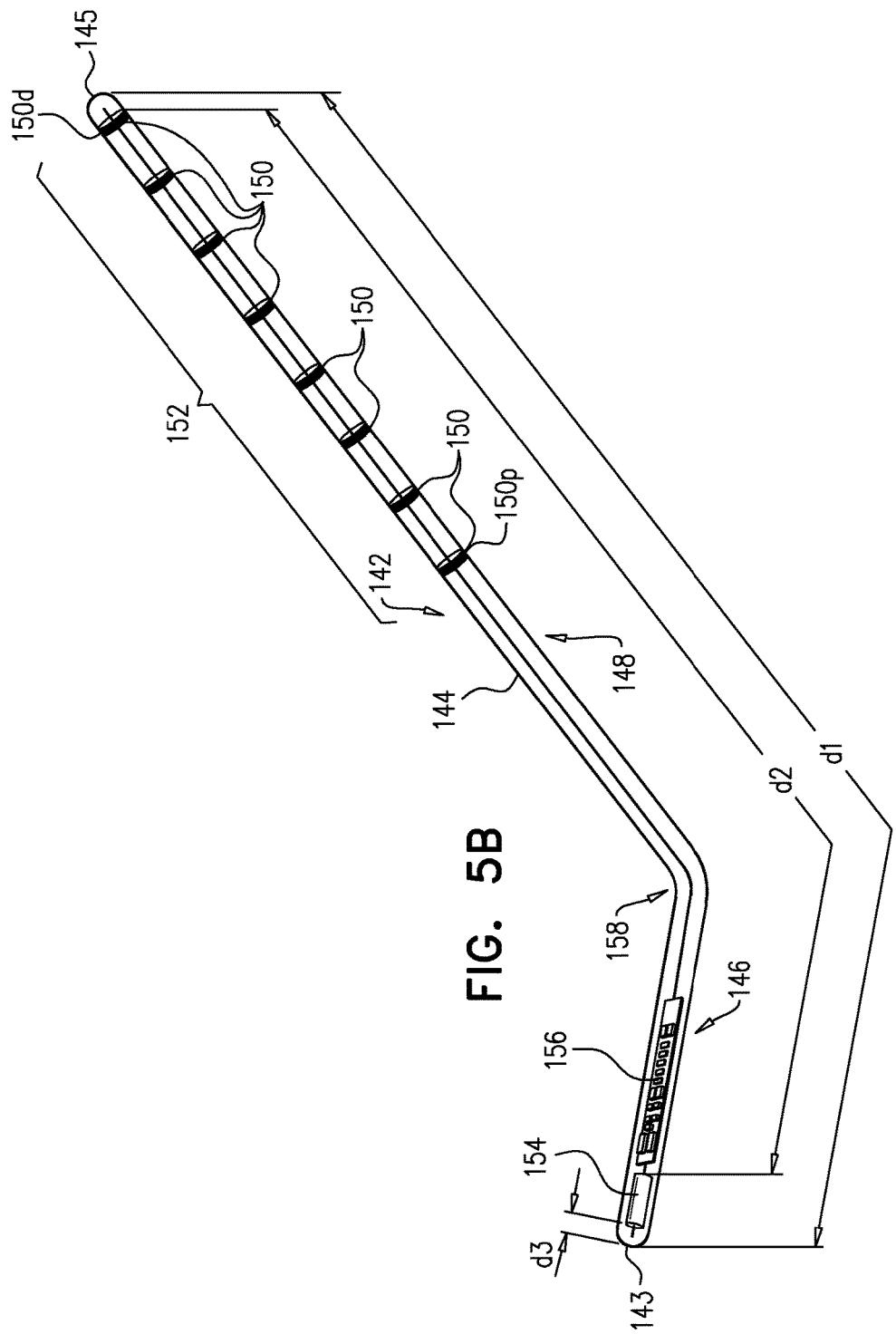

Reference is made to FIGS. 5A-C and 6, which are schematic illustrations of a system 140, and use thereof, for treating a condition of a subject, in accordance with some applications of the invention. System 140 comprises at least one implant 142 and a portable extracorporeal controller 170, configured to wirelessly power the implant. FIG. 5A shows system 140 positioned for use in treating subject 10, FIG. 5B shows implant 142, FIG. 5C shows controller 170, and FIG. 6 shows some steps in the implantation of implant 142, in accordance with some applications of the invention.

Implant 142 comprises a rod-shaped housing 144 that has a proximal end 143, a distal end 145, and a length d1 therebetween. Length d1 is typically greater than 15 cm and/or less than 40 cm (e.g., 15-40 cm). Housing 144 has a distal portion 148 that extends proximally from distal end 145, and a proximal portion 146 that extends between proximal end 148 and the distal portion. Distal portion 148 is deflectable with respect to proximal portion 146. Typically at least part of portion 148 is flexible, and for some applications all of portion 148 is flexible.

A plurality of implant electrodes 150 is distributed on the outer surface of the housing, defining an electrode region 152 between a proximal-most implant electrode 150p and a distal-most implant electrode 150d. For some applications, within electrode region 152 there are greater than 4 implant electrodes and/or less than 8 implant electrodes, e.g., 4-8 implant electrodes, such as exactly 4 implant electrodes or exactly 8 implant electrodes. Typically, region 152 is disposed entirely within distal portion 148. An implant antenna 154 is disposed within proximal portion 146, and a distance d2 of at least 15 cm (e.g., 15-40) cm (measured along the housing) exists between the antenna and distal-most electrode 150d. Typically, a distance d3 between proximal end 143 and antenna 154 is less than 1 cm (measured along the housing). Implant circuitry 156, typically comprising or defining a control unit, is also disposed within housing 144, typically within proximal portion 146. Antenna 154 is configured to receive wireless power, and circuitry 156 is configured to use the received wireless power no drive one or more of electrodes 150 to apply a current that treats the condition of the subject. Typically at least part of portion 146 is rigid, such as where antenna 154 and/or where circuitry 156 is disposed. For some applications portion 146 is entirely rigid. Typically portion 146 is 1-3 cm long (e.g., about 2 cm long). For some applications, a deflection point 158 about which portions 146 and 148 are deflectable with respect to each other is 30-70 cm from proximal end. 143 (measured along the housing).

System 140 is configured to provide spinal cord stimulation to treat pain experienced by the subject. Responsively to antenna 154 receiving wireless power from controller 170, implant circuitry 156 uses the received power to drive electrodes 150 to apply current to the spinal cord 18, in a similar manner to other controller-implant pairs described herein.

The transverse cross-sectional shape of housing 144 is generally uniform along length d1. That is, a transverse cross-section of housing 144 (i.e., a cross-section that is transverse to length d1) taken at one longitudinal site of the housing typically has similar dimensions to any other transverse cross-section taken at any other longitudinal site of the housing. Implant 142 is typically delivered via a needle (e.g., see FIG. 6), and the uniform cross-sectional shape typically facilitates such delivery. Typically these transverse cross-sections have a diameter of more than 1 mm and/or less than 3 mm, such as 1-3 mm. Implant 142 typically comprises no battery, which facilitates housing 144 having the uniform cross-sectional shape.

FIG. 5A shows implant 142 having been implanted in subject 10, in accordance with some applications of the invention. At least part of distal portion 148 (typically including all of electrode region 152) is disposed within the spinal canal 14, typically within the epidural space 16. Proximal portion 146 is disposed at least, partly laterally from portion 148, and is further typically disposed more superficially and/or more inferiorly than is portion 148. For example, and as shown, implant 142 may be implanted such that it extends medially and superiorly from proximal end 143 toward electrode region 152, e.g., such that progressively distal portions of proximal portion 146 are progressively medial, superior, and deeper. For some applications, in this position proximal portion 146 is disposed at an angle of 30-60 degrees with respect to distal portion 148. This positioning of proximal portion 46, and thereby of antenna 154, is hypothesized to facilitate more efficient power transfer from controller 170 to antenna 154, compared to if the antenna were disposed closer to the site at which electrodes 150 are disposed. This positioning also facilitates placement of controller 170 inferiorly to electrodes 150 (e.g., at the level of the lumbar region), which is hypothesized to be more comfortable.

FIG. 6 snows some steps in the implantation or implant 142, in accordance with some applications of the invention. As described hereinabove, implant 142 is typically delivered via a needle for other delivery tube) 192. Typically, this needle is percutaneously advanced along the path along which proximal portion 146 will eventually be disposed, and into the spinal canal (e.g., into the epidural space), via a spinal entry point such as an intervertebral foramen 15 (step 1). For some applications needle 192 comprises a standard epidural needle (e.g., a Tuohy needle, a Crawford needle, a Hustead needle, or a. Weiss needle). Distal portion. 148 of implant. 142 is advanced out of the distal end of the needle and along the spinal cavity, such that electrode region 152 is disposed alongside spinal cord 18 (step 2). The needle is subsequently withdrawn, exposing progressively proximal regions of implant 142 (step 3). For some applications a flexible sheath is first advanced out of the distal end of the needle and along the spinal canal, and the advancement of electrode region 152 along the spinal canal is performed within the sheath.

It is hypothesized that the use of a standard epidural needle and/or techniques similar to those for administering a standard epidural anesthetic, facilitates familiarization, of medical practitioners with the techniques described herein. Furthermore, unlike spinal nerve stimulators that comprise and/or utilize subcutaneous Implantable Pulse Generator (IPG) that comprises a battery (and is typically bulbous), implant 142 is typically implantable in its entirety percutaneously via a needle, and it is typically not necessary to create a subcutaneous pocket.

For some applications, before implant 142 is fully deployed from the needle (e.g., before the needle is fully withdrawn from proximal end 143 of the implant) the position of electrodes 150 is tested by wirelessly powering the implant, e.g., such that the implant behaves as it would after implantation (e.g., as shown in step 3 of FIG. 6). A response to the application of the current by the implant, such as relief of pain, is observed, and the operating physician determines whether to fully deploy, reposition, or withdraw the implant. Step 4 shows implant 142 in place after removal of needle 192 from the subject.

As shown in FIG. 5A, for some applications more than one implant 142 is implanted in subject 10. The electrode regions 152 of each implant 142 may or may not be aligned with each other.

As described hereinabove, extracorporeal controller 170 is configured to wirelessly power implant 142. Extracorporeal controller 170 is typically worn by the subject, e.g., comprising a belt 178 (or being coupled to a belt) that extends around the subject. Controller 170 comprises a battery 172, at least one antenna. 174, and a control unit 176 configured to use power from the battery to drive antenna 174 to transmit wireless power (i.e., a wireless power signal) that will be used by implant 142. For applications in which two implants 142 are as controller 170 typically comprises at least two antennas 174; each configured and positionable to transmit wireless power to a respective implant. For some such applications, a single control unit 176 typically drives both antennas 174, and is typically configured to control each antenna independently.

Controller 170 comprises at least one housing 180 that houses antennas 174, battery 172 and control unit 176. For some applications, two discrete housings 180 are provided; one for each antenna 174. For some applications, and as shown, housing 180 defines two antenna units 182 (e.g., antenna unit 182a and antenna unit 182b). For some applications, antennas 174 are movable with respect to each other, e.g., within housing 180, and/or by moving antenna units 182 with respect to each other. For example, housing 180 may comprise an adjustment mechanism. 184, such as a rack and pinion (e.g., as shown), a ratchet, or any other suitable mechanism. This adjustment allows the juxtaposition between antennas 174 to correspond to the juxtaposition of antennas 154 of implant 142, thereby facilitating efficient control of both implants 142 by controller 170. Adjustment mechanism 184 is shown in FIG. 5C as adjusting a horizontal distance between antenna units 182, but it is to be noted that adjustment mechanism 184 (and/or another adjustment mechanism) may alternatively or additionally be used to move the antenna units vertically with respect to each other and/or with respect to housing 180. ("Horizontal" in this context refers to the medial-lateral anatomical direction, and "vertical" in this context refers to the cranial-caudal anatomical direction.)

For some applications, one or more housings 180 are couplable to belt 178 at different sites, e.g., at a position determined to be most effective for the subject. For example, belt 178 may define a plurality of housing-coupling sites that each facilitates coupling of a housing 180 thereto.

In FIG. 5C, view A is a cutaway of housing 180 that shows internal components, and view B shows a view of a skin-facing face 181 of controller 170 (e.g., of housing 180). For some applications, one or more electrodes 190 are disposed on skin-facing face 181. For some applications electrodes 190 comprise electromyographic (EMG) electrodes, and control unit 176 is configured to receive an EMG signal from the EMG electrodes. For some such applications, control unit 176 is configured to drive antenna 174 to transmit the wireless power in response to detecting a particular EMG signal, such as an EMG signal that is indicative of pain and/or spasm. For some applications controller 170 comprises motion sensor (e.g., accelerometer) 186 and/or a gyroscope 188, and control unit 176 is configured to gate the driving of wireless power in response to detected acceleration and/or orientation. For example, control unit 176 may be configured to not drive the wireless power in response to the detected EMG signal if the detected acceleration and/or orientation is indicative of walking and/or bending (e.g., thereby driving the wireless power only when the EMG signal is indicative of muscle activity due to pain and/or spasm).

The dimensions and positioning of implant 142 are such that when housing 180 (e.g., antenna 174 thereof) is placed directly over antenna. 154 so as to power implant 142, electrodes 190 of the housing are disposed on a skin site that is typically not directly superficial to electrodes 150. For some applications, the skin site is directly superficial to at least one muscle of a myotome that is served by nerve fibers that originate from a nerve in the vicinity of electrodes 150 (e.g., a nerve that is within 5 mm of at least one electrode 150). The positioning of housing 180 over antenna 154 in order to transmit power to the antenna may thereby also facilitate detection, of an EMG signal that results from activity of the nerve fibers that originate from the vicinity of electrodes 150, and responsive stimulation of those nerve fibers. Alternatively or additionally, the skin site may be directly superficial to at least one muscle of a myotome that is not served by nerve fibers that originate from the vicinity of electrodes 150.

Alternatively or additionally, electrodes 190 may comprise Transcutaneous Electrical Nerve Stimulation (TENS) electrodes, and control unit 176 is configured to drive the TENS electrodes to apply a TENS treatment current to the skin of the subject. For example, the TENS current may have a frequency of 10-100 Hz and/or an amplitude of 1-15 mA.

For some applications, the dimensions and positioning of implant 142 are such that antenna 154 is disposed below skin belonging to a dermatome that is served by nerve fibers that originate from the vicinity of electrodes 150 (e.g., a nerve that is within 5 mm of at least one electrode 150). Therefore, the positioning of housing 180 over antenna 154 in order to transmit power to the antenna places electrodes 190 on a skin site within the dermatome that is served by the nerve fibers that originate from the vicinity of electrodes 150. For such applications system 140 therefore facilitates pain relief at one site both via spinal cord stimulation and via TENS. For some applications, the skin site is within a dermatome that is not served by nerve fibers that originate from the vicinity of electrodes 150. For such applications, system 140 therefore facilitates pain relief at one site via spinal cord stimulation, and at another site via TENS.

For some applications, control unit 176 is configured to heat and/or cool at least a portion of skin-facing face 181 of housing 180. For example, housing 180 may comprise an electric heater (e.g., comprising a resistive heating element) and/or a thermoelectric cooling device (e.g., a Peltier cooler).

For some applications, other portable controllers described herein may use electrodes 190, mutatis mutandis.

For some applications, system 140 may comprise a second controller, such as controller 50, described hereinabove. For some such applications, implant 142 is configured to wirelessly powered by controller 50 as described for implant 30, mutatis mutandis. For some such applications, controllers 170 and 50 are configured to interface and communicate (e.g., wirelessly), such as described for controllers 40 and 50, mutatis mutandis.

Reference is again made to FIGS. 5C and 3A. For some applications, controller 82 comprises motion sensor 186 and/or gyroscope 188, and in addition to detecting a position of controller 82 with respect to implant 81, system 80 is configured to map the surface of the part of the body in which the implant is disposed, as the controller is moved over the surface of the part of the body. For such applications, the resulting map is displayed on display 92, along with the position and/or orientation of implant 81 with respect to the mapped anatomy. This is hypothesized to further facilitate optimal placement of controller 82 with respect to implant 81.

Reference is again made to FIGS. 1A-2, and 5A-6. It is no be noted that, for some applications, apparatus and techniques described with reference to system 20 may be combined with those described with reference to system 140. For example, for some applications, implant 142 may be additionally powerable by a mains-powered extracorporeal controller, such as controller 50 of system. 20 (and portable extracorporeal controller 170 may correspond to controller 40 of system 20). For some such applications, the described differences between controllers 40 and 50 with regard to (i) portability, (ii) wireless, power reception efficiency, (iii) duration of transmission in the absence of user input, (iv) proportion of sleeping/wakeful period during which power is transmitted, and treatment current strength, may apply to system 140, mutatis mutandis.

For some applications, the apparatus and techniques described herein may be used in combination with one or more of those described in the following references, all of which are incorporated herein by reference:

U.S. Pat. No. 8,788,045 to Gross et al., filed Jun. 8, 2010, and entitled "Tibial Nerve Stimulation";

U.S. Pat. No. 8,755,893 to Gross et al., filed. Mar. 14, 2013, and entitled "Tibial Nerve Stimulation";

PCT Patent Application Publication WO 2013/111137 to Gross et al., filed Jan. 24, 2013, and entitled "Wireless Neurostimulators"; and PCT Patent Application Publication WO 2014/087337 to Gross et al., filed Dec. 3, 2013, and entitled "Delivery of Implantable Neurostimulators";

A U.S. patent application to Oron et al., filed on even date herewith, and entitled "Anchors and implant devices"; and A U.S. patent application to Plotkin et all, filed on even date herewith, and entitled. "Transmitting Coils for Neurostimulation".

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a condition of a subject, the apparatus being for use with a cellphone, the apparatus comprising:
a first controller, having a mass of 10-500 g and a volume of 25-250 cm^3, and comprising:
at least one first-controller antenna configured to transmit a first wireless power signal having a first signal power;
a cellphone-interfacing antenna, configured to communicate with the cellphone;
a battery configured to store battery power;
a first-controller control unit configured to use the battery power to drive the first-controller antenna to transmit the first wireless power signal;
a user input device, operable by the subject to power the first-controller control unit using the battery; and
a second controller, comprising:
at least one second-controller antenna, configured to transmit a second wireless power signal having a second signal power;
a mains electricity connector; and
a second-controller control unit, configured to use power from the mains electricity connector to drive the second-controller antenna to transmit the second wireless power signal; and
an implant, configured to be implanted in tissue of the subject, the implant comprising:
one or more tissue-contacting electrodes, configured to be placed in contact with the tissue;
at least one implant antenna configured to receive 1-10 percent of the first signal power of the first wireless power signal, and to receive 0.01-1 percent of the second signal power of the second wireless power signal; and
circuitry configured (i) to be powered by the received 1-10 percent of the first signal power, and to responsively drive the one or more electrodes to apply a current, and (ii) to be powered by the received 0.01-1 percent of the second signal power, and to responsively drive the one or more electrodes to apply the current,
wherein:
the circuitry of the implant is configured, in response to receiving the first wireless power signal, to transmit a first juxtaposition signal that includes information indicative of a juxtaposition between the implant and the first controller, and
the first controller is configured to receive the first juxtaposition signal, and to responsively drive the cellphone-interfacing antenna to transmit a second juxtaposition signal that (i) includes information indicative of the juxtaposition between the implant and the first controller, and (ii) is receivable by the cellphone.

2. The apparatus according to claim 1, wherein the first controller is capable, on a single charge of the battery, to drive the first-controller antenna to transmit the first wireless power signal for a total wireless power transmission time that is less than 3 hours.

3. The apparatus according to claim 1, wherein the implant does not comprise a non-transient power storage element.

4. The apparatus according to claim 1, wherein:
the implant comprises a sensor,
the circuitry is configured to power the sensor responsively to the power received by the implant antenna,
the sensor is configured to, when powered by the circuitry responsively to the power received by the implant antenna, detect a factor related to the condition of the subject, and
the circuitry is further configured to receive a signal from the sensor, and drive the one or more electrodes to apply the current at least in part responsively to the power received by the implant antenna, and at least in part responsively to the received signal.

5. The apparatus according to claim 1, wherein the first controller is a hand-held controller.

6. The apparatus according to claim 1, wherein the implant is injectable, and has a longitudinal axis and a cross-sectional area, transverse to the longitudinal axis, of 0.5-3 mm^2.

7. The apparatus according to claim 1, wherein the implant antenna is configured to receive the 1-10 percent of the first signal power while (i) the implant is implanted in the tissue, (ii) the first controller is disposed against skin of the subject directly superficially to the implant, and (iii) the first-controller control unit drives the first-controller antenna to transmit the first wireless power signal.

8. The apparatus according to claim 7, wherein the implant antenna is configured to receive the 0.01-1 percent of the second signal power while (i) the implant is implanted in the tissue, (ii) the subject is lying on a bed in which the second controller is disposed, and (iii) the second-controller control unit drives the second-controller antenna to transmit the second wireless power signal.

9. The apparatus according to claim 1, wherein the second-controller control unit has a longest period of power transmission with no user input, that is at least 1 hour.

10. The apparatus according to claim 9, wherein the second-controller control unit has a longest period of power transmission with no user input, that is at least 2 hours.

11. The apparatus according to claim 9, wherein the first-controller control unit has a longest period of power transmission with no user input, that is less than 1 hour.

12. The apparatus according to claim 11, wherein the first-controller control unit has a longest period of power transmission with no user input, that is less than 10 min.

13. The apparatus according to claim 1, wherein the first controller is incapable of powering the implant when a distance between the first-controller antenna and the implant antenna is greater than 10 cm.

14. The apparatus according to claim 13, wherein the second controller is capable of powering the implant when a distance between the second-controller antenna and the implant antenna is greater than 20 cm.

15. The apparatus according to claim 1, wherein the first controller and the second controller are configured to communicate therebetween information regarding a transmission of wireless power selected from the group consisting of: a transmission of the first wireless power signal, and a transmission of the second wireless power signal.

16. The apparatus according to claim 15, wherein the second controller is configured to configure at least one transmission of the second wireless power signal responsively to receiving, from the first controller, information regarding at least one transmission of the first wireless power signal.

* * * * *

UNITED STATES PATENT AND TRADEMARK OFFICE
CERTIFICATE OF CORRECTION

| | |
|---|---|
| PATENT NO. | : 9,764,146 B2 |
| APPLICATION NO. | : 14/601626 |
| DATED | : September 19, 2017 |
| INVENTOR(S) | : Gur Oron et al. |

It is certified that error appears in the above-identified patent and that said Letters Patent is hereby corrected as shown below:

On the Title Page

Under Inventors, please correct the first inventor from "Guri Oron" to --Gur Oron--

Signed and Sealed this
Twenty-seventh Day of September, 2022

Katherine Kelly Vidal
*Director of the United States Patent and Trademark Office*